United States Patent
Bewick-Sonntag et al.

[11] Patent Number: 5,836,929
[45] Date of Patent: Nov. 17, 1998

[54] ABSORBENT ARTICLES

[75] Inventors: Christopher Phillip Bewick-Sonntag, Kelkheim/Ts; Manfred Plischke, Steinbach/Ts; Mattias Schmidt, Idstein, all of Germany

[73] Assignee: The Procter & Gamble Company, Cincinnati, Ohio

[21] Appl. No.: 569,068

[22] PCT Filed: Jun. 27, 1994

[86] PCT No.: PCT/US94/07203

§ 371 Date: Jan. 17, 1997

§ 102(e) Date: Jan. 17, 1997

[87] PCT Pub. No.: WO95/01147

PCT Pub. Date: Jan. 12, 1995

[30] Foreign Application Priority Data

Jun. 30, 1993 [EP] European Pat. Off. .............. 93305150
Dec. 1, 1993 [EP] European Pat. Off. .............. 93309614

[51] Int. Cl.[6] .............................. A61F 13/15; A61F 13/20
[52] U.S. Cl. ............................................. 604/368; 604/378
[58] Field of Search ...................... 604/368, 369, 604/372, 374, 378, 382, 385.1

[56] References Cited

U.S. PATENT DOCUMENTS

| | | | |
|---|---|---|---|
| 4,338,371 | 7/1982 | Dawn et al. | 428/283 |
| 4,699,823 | 10/1987 | Kellenberger et al. | 428/219 |
| 4,988,823 | 1/1991 | Kaulen | 549/14 |
| 5,176,668 | 1/1993 | Bernardin | 604/368 |
| 5,236,427 | 8/1993 | Hamajima et al. | 604/378 |
| 5,304,161 | 4/1994 | Noel et al. | 604/378 |
| 5,399,371 | 3/1995 | Harris | 426/611 |

FOREIGN PATENT DOCUMENTS 0 401 189 B2 12/1990 European Pat. Off. .
WO 92/11831 7/1992 WIPO .

Primary Examiner—John G. Weiss
Assistant Examiner—Ki Yong O
Attorney, Agent, or Firm—Carl J. Roof; E. Kelly Linman; Jacobus C. Rasser

[57] ABSTRACT

A diaper or other absorbent article may include an absorbent body comprising in sequence from the top (the surface adjacent the wearer's body). An upper assembly (2, 3, 4, 5) comprising an acquisition layer (3) formed of first fibrous material substantially free of superabsorbent material, a superabsorbent layer (5) consisting substantially only of first superabsorbent material having a Gel Layer Permeability value of at least about 4 ml/cm$^2$/sec and which is present in an amount of about 20 g/m$^2$ to 320 g/m$^2$, a storage assembly (6, 7, 8) that includes second superabsorbent material (7) having an absorption against pressure of at least 15 g/g at 50 g/cm$^2$ and which comprises an upper storage layer (6) and a lower storage layer (7) containing at least 70% by weight of the total amount of second superabsorbent in the upper and lower storage layers and which has a thickness which is the same as or less than the thickness of the upper storage layer (6).

26 Claims, 6 Drawing Sheets

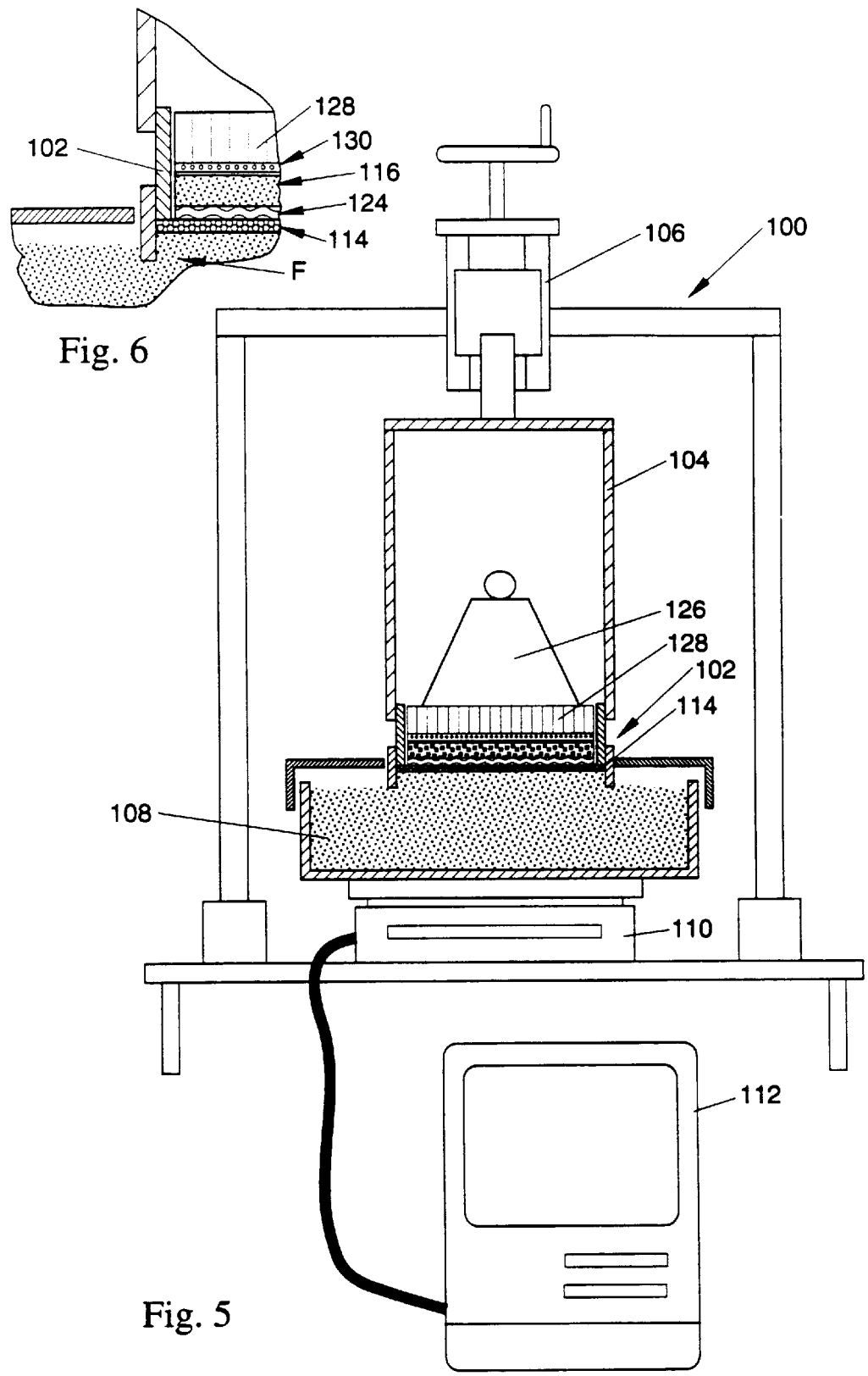

ABSORBENT ARTICLES

FIELD OF THE INVENTION

This invention relates to absorbent bodies comprising fibrous material and superabsorbent material whereby the absorbent bodies can handle relatively large amounts of discharged body fluids, as well as absorbent articles including such bodies, for instance disposable diapers, incontinence articles and training pants.

BACKGROUND OF THE INVENTION

Absorbent articles of this kind generally comprise a liquid pervious topsheet that is located adjacent the wearer's body, a liquid impervious backsheet that is located distant from the wearer's body and adjacent the wearer's clothing, and an absorbent core or other body interposed between the liquid pervious topsheet and the liquid impervious backsheet.

It is well established that the construction of the article, and in particular the construction of the absorbent body, should desirably be such that the article is capable of rapidly acquiring and distributing relatively large volumes of body liquid initially discharged on to the topsheet, and of storing such discharges. It is also desirable that the absorbent body should not release stored liquid when subjected to pressure or prolonged storage. For instance the absorbent body should be such as to minimise rewetting of the topsheet by discharge of liquid that has been stored in the body.

In order to promote distribution of liquid discharges throughout the body, it is desirable to construct the body so that the discharges are transported away from the area of initial deposition, both laterally (in the XY plane) and vertically (in the Z direction).

It is known that different fibrous and other materials promote different performance characteristics. For instance it is known that a relatively low density stiff and/or hydrophobic fibrous structure may serve as a useful upper acquisition layer for rapidly acquiring and distributing liquid discharges, but that such a material may have inadequate storage properties.

It is known that the inclusion of superabsorbent material (often alternatively referred to as polymeric gelling material, hydrogel-forming material or superabsorbent polymer) can be included in absorbent bodies so as to result in a significant increase in the storage capacity. However it is also known that the use of significant amounts of superabsorbent material may tend to be accompanied by a phenomenon referred to as gel blocking. Gel blocking occurs when the superabsorbent material swells in such a manner as to reduce significantly the rate of permeation of liquid that has been applied to the absorbent structure. This can be minimised by appropriate techniques for incorporating the superabsorbent material within a fibrous matrix (for instance as described in U.S. Pat. No. 4,610,678 issued to Weisman & Goldman 9th Sep. 1986) and improved quality superabsorbent materials available in recent years has also reduced the problem. However it can still be a significant problem, particularly when it is desired to incorporate a high density of superabsorbent material in a small volume, i.e., as a layer consisting wholly or mainly of superabsorbent material.

It is desirable to construct the absorbent body such that it has high absorption capacity per unit volume, and in particular such that it has good absorption properties despite being relatively thin.

In order to attempt to obtain optimum properties, there have been numerous proposals in the literature for manufacturing multi-layer absorbent bodies utilising various combinations of fibres and superabsorbent materials.

For instance in WO91/11163 an absorbent body is described comprising, inter alia, a particular type of upper fluid acquisition and distribution layer and a lower layer containing superabsorbent material. Additionally, there have been many proposals to incorporate at least two layers which include superabsorbent material. In some instances the same material is used in both layers but in other instances different superabsorbent materials are proposed. For instance in U.S. Pat. No. 4,338,371 issued 6th Jul. 1982 to Dawn an absorbent body is proposed comprising, inter alia, an upper wicking layer, a fibrous layer, a layer of acrylic carboxylate superabsorbent polymer, and a lower (distant from the wearer's body) layer comprising hydrolysed starch acrylonitrile graft superabsorbent polymer. It is stated that the lower layer of superabsorbent material should gel faster than the upper layer, and that the upper layer should gel slower and absorb more fluid than the lower layer.

In EP-B-401189 it is proposed that there should be mutually different superabsorbents disposed in at least two layers wherein one of the absorbents has a high absorption rate and the other has a high liquid-retention ability when subjected to pressure. It is recommended that the fast-absorbing superabsorbent should be located in the lower layer (distant from the wearer's body).

In WO92/11831 a multi-layer absorbent article is described which can include at least one acquisition/distribution layer and, beneath each such layer, a layer comprising superabsorbent material. Each of the layers is characterised in that the superabsorbent material has a fast absorption rate. This publication acknowledges that the provision of a plurality of such layers may prevent travel of body liquids through the entire absorbent body because of the tendency for a layer containing such superabsorbent material to block the flow of liquid. WO92/11831 proposes the provision of particular pathways to allow flow despite such blockage.

A wide variety of superabsorbent materials are commercially available and they are, and have been, supplied to meet a wide variety of requirements. For instance different materials are available which have, for instance, fast or slow rates of absorption, high or low gel strengths, high or low absorption against pressure and so forth.

Despite the wide variety of superabsorbent and fibrous materials, and combinations thereof, that have been proposed, there remains a need to try to improve the construction of absorbent bodies for incorporation in, for instance, diapers so as to optimise performance, especially having regard to the desirable objective of minimising the thickness of the absorbent body while maximising acquisition, storage and retention with lowest possible rewet results during use.

It has been our object to provide novel absorbent bodies which overcome various of the disadvantages of existing absorbent bodies and in particular that permit the attainment of particularly good absorption characteristics and which are easy to manufacture by conventional techniques.

SUMMARY OF THE INVENTION

The invention provides an absorbent body comprising in sequence from the top (i.e., the surface that is to be adjacent to the wearer's body):

an upper assembly comprising an acquisition layer substantially free of superabsorbent material and a superabsorbent layer consisting mainly of first superabsorbent material and which has a Gel Layer Permeability (GLP) value of at least about 4 and generally at least about 6, and preferably at least 9 and most preferably at least 15,×10$^{-7}$ cm$^3$sec/g and which is present in an amount of at least about 20 g/m$^2$ and a lower assembly that includes second superabsorbent material having an Absorption Against Pressure of at least 15 g/g (and preferably at least 20 g/g) at 50 g/cm$^2$ and which comprises an upper layer having void space for storage and redistribution of liquid discharges (e.g., urine or menstrual fluid) and a lower layer which contains second superabsorbent material and wherein at least 70% by weight of the total amount of the second superabsorbent material which is in the upper and lower layers is in the lower half of the combined thickness of the upper and lower layers.

In one important aspect of the invention, the first and second superabsorbent materials are the same material. This facilitates manufacture and can give good performance.

In another important aspect of the invention the first and second superabsorbent materials are different materials which have different properties, and in particular the second superabsorbent material preferably swells faster than the first material.

The invention also includes absorbent articles comprising, in sequence, a liquid pervious topsheet, an absorbent body as defined above arranged with the upper acquisition layer towards the topsheet, and a liquid impervious backsheet. Preferred absorbent articles of the invention include disposable diapers, incontinence articles and training pants.

BRIEF DESCRIPTION OF THE DRAWINGS

FIG. 5 is a part sectioned side view of apparatus used in the X,Y-Demand Absorbency Test.

FIG. 6 is an enlarged view of a portion of FIG. 4.

FIGS. 2 to 8 relate to Test Methods described below.

Referring to FIGS. 1a, b and c, the exemplary article 1 is a diaper or other absorbent article comprising a topsheet 2 (which contacts the body of the wearer), a backsheet 9 and the novel absorbent core of the invention between the topsheet and the backsheet.

Figure 1A:
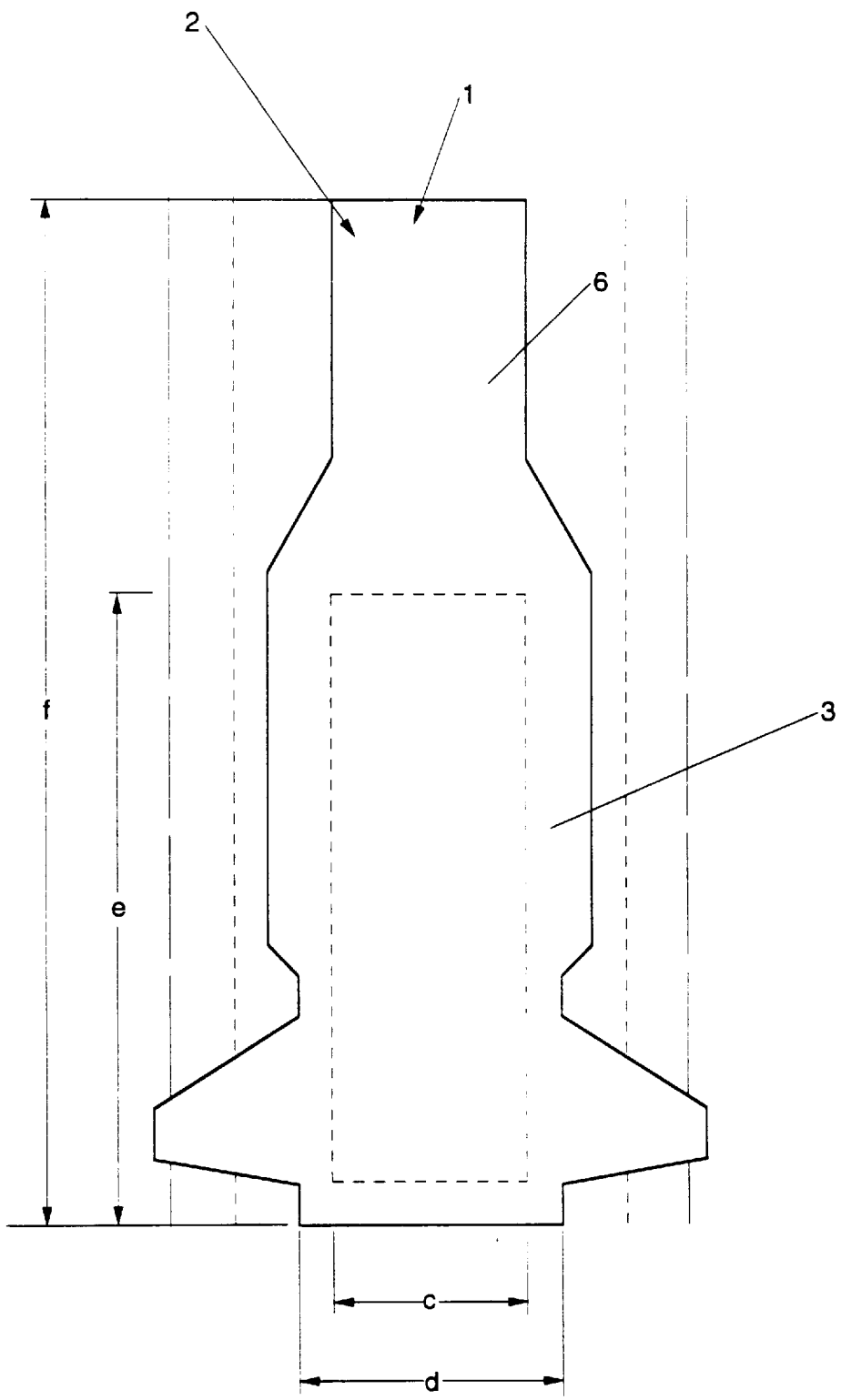
FIG. 1a is a diagrammatic plan view of an exemplary absorbent article according to the present invention.

The core comprises an upper acquisition/distribution layer 3, a superabsorbent layer 5 of first superabsorbent material separated from the acquisition layer 3 by a tissue layer 4 having two folds in the Z direction, an upper fibrous layer 6 and a lower layer 7 comprising second superabsorbent material, and a tissue layer 8. The layers 6 and 7 may be separate layers as shown diagrammatically or they may merge into a single layer and they serve as a storage and redistribution assembly. As will be apparent from the drawings, it is not essential that the layers should be co-extensive.

DETAILED DESCRIPTION OF THE PREFERRED EMBODIMENTS OF THE INVENTION

It is thought that the combination of materials and layers defined in the invention provides a useful optimisation of the functionalities of the materials. In particular, it is thought to allow saturation of the superabsorbent material first in the region of the core furthest away from the wearer's body, and then gradually closer to the wearer's body until the core has reached its maximum capacity. The invention achieves this by providing an upper assembly or structure which acts initially as an acquisition/distribution structure and that is relatively permeable to body discharges. The discharges therefore pass relatively quickly through the first layer of superabsorbent, and into the lower assembly which acts as a storage and redistribution assembly where the liquid can be stored. By preferentially arranging the second superabsorbent material in the lower part of the lower assembly, so that the upper part has a lower or zero concentration of superabsorbent material, void space is provided in the lower assembly that can promote the storage capacity of that assembly. By using second superabsorbent material having the defined Absorption Against Pressure value, good storage retention is achieved.

Liquid that is not adequately absorbed into the second superabsorbent material can subsequently be absorbed in the first superabsorbent material. The provision of this as a layer beneath the acquisition/storage layer has the advantage that this first superabsorbent material acts to dry out the acquisition layer so as to optimise rewet and to improve skin dryness.

In order to achieve the desired performance characteristics it is necessary to select appropriate combinations of various materials in the core, as well as their amounts. The following description refers to suitable materials and by subjecting appropriate test articles made from them to the specified tests, and modifying the articles when necessary to achieve the required test results, cores according to the invention can be achieved.

For instance to achieve the above described fluid handling advantages the first assembly should be sufficiently open, or permeable, relative to the second structure to allow quick passage of body discharges through the first structure and into the second structure. However, the first structure should not be too open as this could lead to a higher risk of gel-blocking of the superabsorbent material in the second structure, thereby under-utilising the absorbent capacity in that structure. A balance should be struck.

Upper Assembly

This comprises an acquisition layer and a layer of first superabsorbent.

The acquisition layer is the upper effective layer of the absorbent core or other body (excluding any tissue or topsheet if present). It is generally substantially free of superabsorbent material. If superabsorbent material is included, the amount should be kept low (for instance as in WO91/11163) but preferably the layer is wholly free of superabsorbent material, at least in the upper half, and generally throughout most or all of its thickness. The layer may be of foam or other suitable porous or capillary material but is usually formed of first fibrous material.

Suitable materials and properties of this upper layer, and methods of making it, are described in WO91/11163.

This upper layer preferably has a Wet Compressibility of at least about 5 cm$^3$/g and a Drip Capacity of at least 10 g/g. Fibrous material of the defined Wet Compressibility and the defined drip capacity maintains its openness, or void volume, when wetted by, for example, urine. The provision of such a permanently open fibrous layer having a high drip capacity in the core means that not only does the core acquire body discharges, such as urine, rapidly, but the layer also has the potential to transfer these discharges into the subjacent structure of first particulate superabsorbent material relatively quickly.

The first fibrous material can be any fibrous material that has a suitable resistance to load when wet, i.e. is able to maintain satisfactory void volume under such conditions and this is defined herein as Wet Compressibility which is measured by the Wet Compressibility test described below.

The "Wet Compressibility", or void volume per gram of wetted fibrous material under a 77.5 gcm$^{-2}$ (1.1 psi) load, of the first fibrous material is preferably at least 5 cm$^3$g$^{-1}$, preferably at least 6 cm$^3$g$^{-1}$, and most preferably at least 6.5 cm$^3$g$^{-1}$, e.g., up to 8 or even 10 cm$^3$g$^{-1}$ or more.

The first fibrous material preferably has a "Drip Capacity" of at least 10 ml g$^{-1}$, preferably at least 15 ml g$^{-1}$, and most preferably at least 20 ml g$^{-1}$, e.g., up to 25 or even 30 ml g$^{-1}$. The "Drip Capacity" is a measure of the ability of a fibre matrix to receive synthetic urine at a loading point, transfer it away from that point and then hold it within the matrix. The "Drip Capacity" is measured by the Drip Capacity Test described below.

Suitable first fibrous material can comprise chemically stiffened cellulosic fibres, generally in an amount of 50 to 100% by weight of the first fibrous material and 0 to 50% by weight other fibres such as non-stiffened cellulose fibres and synthetic fibres. Preferred chemically stiffened cellulosic fibres are stiffened, twisted, curled cellulosic fibres which can be produced by internally cross-linking cellulose fibres with a cross-linking agent. The types of stiffened, twisted, curled cellulosic fibres useful as the hydrophillic fibre material of the absorbent structures described herein are described in greater detail in the following patents: U.S. Pat. No. 4,822,453 entitled "Absorbent Structure Containing Individualised Cross-linked Fibres", issued to Dean et al. on Apr. 18, 1989; U.S. Pat. No. 4,888,093 entitled "Individualised, Cross-linked Fibres And Process For Making Said Fibres", issued to Dean et al. on Dec. 19, 1989; U.S. Pat. No. 4,889,595 entitled "Process For Making Individualised, Cross-linked Fibres Having Reduced Residuals And Fibres Thereof", issued to Herron et al. on Dec. 26, 1989; U.S. Pat. No. 4,889,596 entitled "Process for Making Individualised Cross-linked Fibres and Thereof", issued to Schoggen et al. on Dec. 26, 1989; U.S. Pat. No. 4,889,597 entitled "Process For Making Wet-Laid Structures Containing Individualised Stiffened Fibres", issued to Bourbon et al. on Dec. 26, 1989; and U.S. Pat. No. 4,898,642 entitled "Twisted, Chemically Stiffened Cellulosic Fibres And Absorbent Structures Made Therefrom", issued to Moore et al. on Feb. 5, 1990.

Instead of using stiffened cellulosic fibres, it is also possible to formulate the layer from synthetic polymer fibres, usually mixtures of synthetic and natural fibres. Suitable fibres are polyethylene, polypropylene, viscose and rayon fibres, and bi-component fibres of these materials, mixed with airfelt, cellulose, modified cellulose (as above) or other natural fibres. Typically such a mixture will have at least about 5% synthetic fibres, and preferably at least about 10% synthetic fibres.

The first fibrous material layer is generally formed by air laying the desired fibres during or prior to the production of the absorbent core, but if desired a preformed non-woven or a wet or air laid or other fibrous material can be used.

The superabsorbent layer consisting mainly of first superabsorbent material may be formed in the lower part of the acquisition layer but preferably is a separate layer and may be separated from the acquisition layer by a tissue or other layer that acts as a containment barrier for the superabsorbent material.

It is important that this layer consisting mainly of first superabsorbent material should allow urine, menstrual fluids or other body discharges that are rapidly acquired by and distributed by the first fibrous layer to pass rapidly through and be distributed beyond the layer of first superabsorbent material without significant blockage by that layer.

The amount of the first superabsorbent material should be sufficient to provide at least a substantially overall layer of superabsorbent material when swollen by absorption of urine in use. The superabsorbent material is usually in particulate form and it is usually necessary for it to be present in an amount of at least about 20 g/m$^2$ in order that it provides a substantially overall layer. Often the amount is at least 50 g/m$^2$.

Generally the layer should not be too thick and normally the amount is below 320 g/m$^2$, often below 200 g/m$^2$.

Lower Assembly

The lower assembly serve as a storage and redistribution assembly and includes an upper, usually fibrous, layer and a layer of second superabsorbent material.

The upper layer in the lower assembly is generally fibrous but can be formed of foam or other suitable capillary or porous material. It provides void space for storage of liquid. The fibrous or other material of this layer can add an extra stage of control to the absorption profile of the absorbent body of the invention. For instance it may slow down the passage of body discharges as they leave the first superabsorbent layer and prior to them reaching the second superabsorbent layer material. This may minimise the chances of gel-blocking occurring in the second superabsorbent material, and this can be particularly useful in those embodiments where the second superabsorbent has faster absorption kinetics and so tends to be more sensitive to this phenomenon.

The second fibrous material may comprise fibrous material of any conventional type. The fibrous material can be airfelt, a mixture of natural and synthetic fibres, chemically cross-linked cellulose fibre or any other known fibrous material commonly used in absorbent cores of absorbent articles. If desired it may include some fibres of the same type as the first fibrous material.

Each fibrous layer may add integrity and may also add softness to the absorbent core.

The upper layer may be substantially or wholly free of superabsorbent material and thus may be an air felt or other fibrous or storage layer formed in the absence of superabsorbent material. The lower layer can then be a separately formed layer comprising second superabsorbent material. The layer may be a blend with fibres or may consist mainly of the superabsorbent material.

However it is often desirable for the upper and lower layers to be formed as in EP-A-198683, wherein the upper and lower layers are provided by an air laid fibrous matrix wherein more than half by weight, and usually at least 70% by weight, of the superabsorbent material in the upper and lower layers is in the lower half of the thickness of the upper and lower layers. For instance 70 to 100%, often 70 or 75 to 90 or 95% by weight of the second superabsorbent material is in the lower 50% of the thickness of the upper and lower layers. There can be some, for instance 5% to 10% or sometimes up to 30%, of the second superabsorbent material in the upper half of the thickness of the upper and lower layers.

Generally the upper and lower layers are provided by air laying a blend of appropriate wood pulp or other hydrophilic fibres for instance on to a conventional air laying drum or other receiving surface. The distribution of superabsorbent material through the thickness of upper and lower storage layers can be achieved by appropriate selection of the distribution of superabsorbent material into the stream of fibres being carried down on to the receiving surface, for instance as described in EP 198683, or by injecting or otherwise distributing the superabsorbent into the air laid matrix as it is formed on the receiving surface.

When air laying such a matrix, it is generally desirable additionally to provide a fibre layer substantially free of superabsorbent material which is air laid with and beneath the lower layer. Instead of or in addition to this a layer of separately formed tissue or other fibrous material may be provided in this position.

Typically the amount of second superabsorbent material is 30 to 95%, preferably 45 to 75%, by weight of the upper and lower layers. Its total weight is typically in the range 100 to 2000 g/m$^2$.

Superabsorbent Materials

One suitable definition of first superabsorbent material which can be included in useful amounts in that layer is the Gel Layer Permeability value (GLP) measured by the GLP test described in the test methods below. The first superabsorbent material should generally have a GLP value of at least 6, preferably at least 9, for instance more than 15 and up to 40,×10$^{-7}$ cm$^3$ sec/g or more.

The objective of the Gel Layer Permeability (GLP) test is to determine the saline flow conductivity of the gel layer formed from a dispersible AGM that is swollen in Jayco synthetic urine under a confining pressure. The flow conductivity provides a measure of the ability of the gel layer formed from a swollen AGM to acquire and distribute fluid during use in an absorbent structure. Darcy's law and steady-state flow methods are used for measuring gel-layer permeability and determining saline flow conductivity. (See, for example, "Absorbency", ed. by P. K. Chatterjee, Elsevier, 1985, Pages 42–43 and "Chemical Engineering Vol. II, Third Edition, J. M. Coulson and J. F. Richardson, Pergamon Press, 1978, Pages 125–127.)

The gel layer used for permeability measurements is formed by swelling an AGM in Jayco synthetic urine for a time period of 60 minutes. The gel layer is formed and its flow conductivity measured in a piston/cylinder apparatus under a mechanical confining pressure of 0.3 psi. The bottom of the cylinder is faced with a No. 400 mesh screen to retain dry-swollen AGM and permit absorption and z-direction transport of urine. The piston is permeable to fluid. Flow conductivity is measured using a 0.118M NaCl solution. For an AGM whose uptake of Jayco synthetic urine versus time has substantially levelled off, this concentration of NaCl has been found to maintain the thickness of the gel layer substantially constant during the permeability measurement. For some AGMS, small changes in gel-layer thickness can occur as a result of AGM swelling, AGM deswelling, and/or changes in gel-layer porosity. A constant hydrostatic pressure of 4920 dyne/cm$^2$ (5 cm of 0.118M NaCl), above the gel layer, is used for the measurement.

Flow rate is determined by measuring the quantity of solution flowing through the gel layer as a function of time. Flow rate may vary over the duration of the experiment. Reasons for flow-rate variation include changes in the thickness of the gel layer and changes in the viscosity of interstitial fluid, as the fluid initially present in interstitial voids(which, for example, can contain dissolved extractable polymer) is replaced with NaCl solution. If flow rate is time dependent, then the initial flow rate, typically obtained by extrapolating the measured flow rates to zero time, is used to calculate flow conductivity. The saline flow conductivity is calculated from the initial flow rate, dimensions of the gel bed, and hydrostatic pressure. For systems where the flow rate is substantially constant, a gel-layer permeability coefficient can be calculated from the saline flow conductivity and the viscosity of the NaCl solution.

Another way of defining useful materials is in terms of the Dynamic Swelling Rate. Suitable materials have a substantially non-decreasing Dynamic Swelling Rate.

The Dynamic Swelling Rate of a superabsorbent material is a measure of the uniaxial swelling of the superabsorbent material in a test tube as synthetic urine is added to it as a function of time. The test method used to measure the dynamic swelling rate is called the Dynamic Swelling Rate Test, and is described below. By saying that the Swelling Rate is substantially is substantially non-decreasing, we mean that the relative deviation of the Swelling Rates, as explained below in the description of the test method, should be less than 50%, preferably less than 25%, more preferably less than 10% and most preferably less than or equal to zero percent.

The first superabsorbent material generally has Absorption Against Pressure value of at least 15, and generally at least 20, g/g at 50 g/cm$^2$. The Performance Under Pressure value is generally more than 20 g/g and preferably more than 30 g/g.

The second superabsorbent material should have an Absorption Against Pressure of at least 15, and preferably at least 20, g/g at 50 g/cm$^2$ (0.7 psi) pressure, The Performance Under Pressure value is generally more than 20 g/g and preferably more than 30 g/g.

Useful results can be obtained when the same material is used as the first and second superabsorbent materials, in which event the first superabsorbent material will have the same Absorption Against Pressure value as the second material. However different materials can be used and in order to optimise performance in some respects, and in particular to obtain greater control in the flow and absorption of urine and other fluid discharges within the core, it can be preferred for the second material to have absorption kinetics which are faster than those of the first superabsorbent material. This is measured in terms of the Dynamic Swelling Rate of each of the superabsorbent materials, wherein the dynamic swelling rate of the first superabsorbent material is preferably not greater than ⅔, and preferably not greater than ⅓, of that of the second superabsorbent material. The alternative way of defining this difference is to say that the Dynamic Swelling Rate of the second superabsorbent material is preferably at least 1.5 times, and most preferably at least 3 times, the Dynamic Swelling Rate of the first superabsorbent material.

It is desirable, especially when the second superabsorbent material has faster absorption kinetics, for it to have a Dynamic Swelling Rate of at least 0.2 grams urine per second per gram of superabsorbent material (g g$^{-1}$ s$^{-1}$). Preferably the Dynamic Swelling Rate of the second superabsorbent material is at least 0.3 g g$^{-1}$ s$^{-1}$ and it can be up to, for instance, 0.6 or even 1 g/g/s.

The first and second superabsorbent materials may be of any suitable physical shape, e.g. fibrous, film or particulate. Preferred materials are particles that may be true spheres, granules, aggregates, agglomerates or irregular shaped particles as typically produced by a grinding process. Typically they are hydrogel-forming polymers which comprise an acrylate polymer or copolymer.

An example of superabsorbent materials having the above described properties is Favor SX (available from Chemische Fabrik Stockhausem GmbH, Krefeld, Germany). In particular, it is desirable to use as the first superabsorbent material Favor SX, Type P, lot no. W51776 available from Chemische Fabrik Stockhausen which have a GLP value of 9×10$^{-7}$ cm$^3$ sec/g.

The particulate superabsorbent material can be substantially entirely polymeric absorbent hydrogel-forming material, or can comprise a mixture of superabsorbent hydrogel-forming material with an additive, such as for example, powdered silica.

The first superabsorbent material, and sometimes also the second superabsorbent material, is provided as a layer which consists mainly of the respective superabsorbent material. By this we mean that at least 50% by weight, and often at least 70 or 80% by weight of the layer is provided by superabsorbent material. Preferably it consists substantially only of superabsorbent by which we mean that the superabsorbent particles should mainly be in contact with each other. This layer of superabsorbent can be bonded to, or otherwise supported by a support sheet. The distribution within the layer can be uniform or can be varied, for example to provide a shaped design which may be striped or profiled within the layer, see for example EP-A217,666 and U.S. Pat. No. 4,935,022.

The layer can consist of superabsorbent material integrated with or dispersed within a support sheet, such as a cellulose-based tissue or other non-woven material. The superabsorbent material may be integrated with the support sheet by bonding or by mechanical means such as embossing or calendering. Alternatively, the preformed layer can consist substantially only of superabsorbent material in the form of permeable sheets or film-like structures. Such sheets or films can be formed during polymerisation of the superabsorbent material, or by bonding together particles or fibres of superabsorbent material by adhesives or other suitable means. For example U.S. Pat. Nos. 5,102,597 and 5,124,188 describe processes of producing sheets of bonded particulate superabsorbent material.

In one embodiment, the same superabsorbent is used as the first and second superabsorbent materials. Accordingly, both materials preferably have a GLP value of at least 6, preferably at least 6.5 and most preferably 7 to 10 or even 12 or 15 ml/cm$^2$/sec.

In another embodiment, the first and second superabsorbent materials have different absorption kinetics, and in particular the second superabsorbent material has faster absorption kinetics than the first superabsorbent material, for instance having a Dynamic Swelling Rate of at least 0.2 gg$^{-1}$s$^{-1}$ and/or a Dynamic Swelling Rate that is preferably at least 1.5 times, and most preferably at least 3 times, the Dynamic Swelling Rate of the first superabsorbent material. The provision of this underlying, rapidly absorbing, second superabsorbent will have the effect of tending to "suck" urine through the upper assembly into the lower assembly.

The consequence of this is that if absorbent bodies according to the invention are made wherein everything is constant except for the Dynamic Swelling Rate of the lower, second, superabsorbent material, the rate of transfer of urine through the upper assembly and down into the lower assembly will tend to increase with an increase in the Dynamic Swelling Rate of the superabsorbent in the lower assembly. Accordingly, another preferred aspect of the invention resides in absorbent bodies wherein the first superabsorbent material has a GLP value lower than may be optimum when the same superabsorbent is used in both layers (for instance having a GLP value of at least 3 or 4 and usually at least 6,×10$^{-7}$ cm$^3$ sec/g) and the second superabsorbent has a Dynamic Swelling Rate at least 1.5 times, and preferably at least 3 times, the Dynamic Swelling Rate of the first superabsorbent, and/or preferably has a Dynamic Swelling Rate of at least 0.2 g/g/s.

When it is desired to have superabsorbents of different absorption kinetics or other properties this can be achieved by using different chemical types or both providing the same chemical type but having different particle sizes or physical shape in the first and second assemblies. Thus, the first superabsorbent material may mainly comprise coarser material and may have a coarser average particle size, and the lower superabsorbent material may mainly comprise finer material and maybe of smaller average particle size.

The use of coarse particles as the first superabsorbent promotes the permeability of the layer of first superabsorbent. The finer particles have a larger surface to volume ratio than coarser particles, and so will tend to be capable of faster absorption than the coarser particles, provided there is no gel blocking. Confining the finer absorbent material to the lower structure also has the advantage of reducing the risk of its escape onto the skin of the wearer and also reducing the risk of pock-marking which can be caused by the coarser particulate superabsorbent material penetrating the impervious backsheet.

The particle size of the superabsorbent material is expressed as a median mass particle size. This is measured by the Sieve Test described below. Generally each is above 50 µm and usually above 100 µm, but below 850 µm and usually below 600 µm. When the first and second superabsorbents are of different sizes the median mass particle size of the first superabsorbent material of the first structure is preferably more than 300 µm (50 mesh), more preferably in the range of 400 to 850 µm (20 to 40 mesh), and most preferably in the range of 600 to 850 µm (20 to 30 mesh). The finer, second, superabsorbent material typically has a median mass particle size of less than 300 µm (50 mesh) but above 50 µm (325 mesh), preferably in the range of 100 to 250 µm (60 to 140 mesh), and more preferably in the range of 150 to 250 µm (60 to 100 mesh).

As an alternative to using superabsorbent materials of different particle sizes to provide any required difference in absorption kinetics between, it is also possible to use different chemical types of superabsorbent material having inherently different absorption speeds. The superabsorbent materials can be different chemical composition, for example cross-linked partly neutralised polyacrylic acid or a starch-based superabsorbent material. Alternatively, they can be different by virtue of their production processes, for example, a "broken-gel process" or an inverse suspension (or bead) polymerisation.

Another way in which the superabsorbent materials may differ chemically is that they may be cross-linked with different cross-linking agents or to different extents, or one of the superabsorbent materials may be surface cross-linked, or they both may be surface cross-linked to different extents.

Absorbent Core Properties

The absorbent core of the invention preferably has an Average Theoretical Basis Capacity of at least 0.7 ml cm$^{-2}$, preferably at least 0.8 ml cm$^{-2}$ and typically up to 1 or 1.2 ml/cm$^2$ or even more.

The Average Theoretical Basis Capacity is calculated by summing the Basis Capacities of the individual components to give the Theoretical Basis Capacity of the core, and then calculating the average per unit area. The Basis Capacity is termed theoretical because for its calculation it requires that the total capacity be broken down into the individual capacities, and also because it is a measurement carried out in the absence of any applied load; the core is often under load in natural use.

In calculating the Average Theoretical Basis Capacity, the Basis Capacity of the superabsorbent material is calculated assuming the "Teabag Retention" capacity. The "Teabag" capacity is measured by the Teabag Retention Capacity Test described below.

In calculating the Average Theoretical Basis Capacity, the absorptive capacity of each of the fibrous materials is measured by the X,Y-Demand Absorbency Test described below. In this test airfelt typically absorbs about 4 g synthetic urine per gram of dry fibres, and chemically cross-linked cellulose as described in U.S. Pat. No. 4,898,642, for example, typically absorbs about 6 g synthetic urine per gram of dry fibres at a pressure of 20 g cm$^{-2}$ (0.3 psi).

The absorbent core of the invention can be made relatively small and thin and compact, and yet can have high absorbency.

The stack height or caliper of the core or other absorbent body of the invention as measured at 200 gcm$^{-2}$ (3 psi) (unless otherwise stated) in a Stack Height Test, described below, is generally not more than 9 mm, and is preferably not more than about 7.5 mm and it can be 5 mm or even less.

The absorbent core preferably has an Acquisition Rate of at least 1.5 ml s$^{-1}$ at 50% of the theoretical basis capacity. Preferably the value is at least 2 ml/sec. It can be up to 5 ml/sec or more. Since the absorbent core of the invention may comprises different amounts of superabsorbent materials in different areas, and may include different superabsorbents, having different absorption kinetics, the fluid acquisition profile of the core may vary from point to point both in the XY plane and in the Z-direction, and will vary during acquisition. It is therefore thought more realistic to measure the acquisition rate at 50% of the total theoretical capacity (rather than at the unused or fully used conditions). This allows an average in-use core performance assessment to be expressed in the acquisition rate measurement.

The Acquisition Rate is measured by the Acquisition Rate Test described below. It simulates the introduction of urine into an absorbent structure and measures the rate at which the structure acquires a load of synthetic urine.

In addition to having good fluid acquisition properties, the absorbent core of the invention has good fluid uptake properties. The core preferably has a Fluid Uptake Rate of at least 0.05 grams urine per second per gram dry material (g g$^{-1}$ s$^{-1}$), and preferably more than 0.06 g g$^{-1}$ s$^{-1}$. It can be up to 0.1 gg$^{-1}$s$^{-1}$ or more. Fluid uptake is a measure of the efficiency of the absorbent core structure to absorb fluid and then readily distribute it. It is the value Xgo/tgo measured by the X,Y-Demand Absorbency Test described below.

A further consequence of the fluid handling and absorption properties of the absorbent core or other body of the invention is apparent from its good rewet properties. The absorbent body the invention can have a Rewet value of no greater than 0.6 g synthetic urine, preferably no greater than 0.3 g, and most preferably no greater than 0.2 g. A low rewet value indicates a high, or efficient, urine retention by the absorbent core, or the absorbent article in which it is incorporated. A high rewet indicates poor urine retention, which may lead to accumulation of urine on the surface of the core or article thereby causing rewetting of the user's garments and/or the user itself. Rewet is measured by the Rewet Test described below.

Manufacture of the Absorbent Body

The absorbent core or other body of the invention can be made by air laying, or by wet laying, the appropriate materials (fibres and superabsorbent) in sequence in conventional manner, or by assembling preformed layers, for example of the superabsorbent materials as described above, or by any suitable combination thereof. For example, GB-A-2,191,793 and GB-A-2,191,515 describe methods of air laying fibrous materials using a rotating drum laydown system, and GB-A-2,175,024 and EP-A-330,675 describe the incorporation of superabsorbent material into the absorbent structures. Combined processes in which some components are air laid and some are introduced as preformed layers can be used.

Additional layers can be incorporated in the absorbent body and, as mentioned above, tissue layers can be incorporated. For instance tissue layer may encapsulate the first superabsorbent material and/or the second superabsorbent material. A tissue layer may be included in or around, for instance, an upper layer in the lower assembly formed of second fibres.

Absorbent Articles

According to a further aspect of the invention an absorbent article comprises a liquid pervious topsheet, a liquid impervious backsheet, and an absorbent core as described above interposed between the topsheet and the backsheet with the first structure positioned towards the topsheet and the backsheet is positioned towards the second structure.

The article may be, for instance, a sanitary napkin but is preferably an incontinence article, a training pant or a disposable diaper. It may be constructed in a conventional manner.

For instance the backsheet may be secured to the absorbent core by attachment means. These means may be a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The adhesive preferably comprises an open pattern network of filaments of adhesive as is disclosed in U.S. Pat. No. 4,573,986 entitled "Disposable Waste-Containment Garment", which issued to Minetola et al on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet should be substantially impervious to liquids (e.g., urine) and is preferably manufactured from a thin plastic film, although other flexible liquid impervious materials may also be used. The backsheet prevents exudates absorbed and contained in the core from wetting articles which contact the absorbent article such as bedsheets and undergarments. The backsheet may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mil). Particularly preferred materials for the backsheet include RR8220 blown films and RR5475 cast films as manufactured by Tredegar Industries, Inc. of Terre Haute, Ind. The backsheet is preferably embossed and/or matte finished to provide a more clothlike appearance. Further, the backsheet may permit vapours to escape from the absorbent core (i.e., breathable) while still preventing exudates from passing through the backsheet.

The topsheet is positioned adjacent the body surface of the absorbent core and is preferably joined thereto and to the backsheet by attachment means such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the article is a diaper wherein topsheet and the backsheet are joined directly to each other in the diaper periphery and elsewhere are indirectly joined by directly joining them to the absorbent core.

The topsheet is compliant, soft feeling, and non-irritating to the wearer's skin. Further, the topsheet is liquid pervious permitting liquids (e.g., urine) to readily penetrate through its thickness. A suitable topsheet may be of natural and synthetic fibres. Preferably, the topsheet is made of a material that is hydrophobic to isolate the wearer's skin from liquids contained in the absorbent core. There are a number of manufacturing techniques which may be used to manufacture the topsheet. For example, the topsheet may be a nonwoven web of fibres spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibres such as Sawabond (trade name) manufactured by Sandler GmbH & Co. KG, Schwarzenbach, Germany.

An absorbent article comprising the absorbent core of the invention generally has a caliper that is substantially the same as the caliper of the absorbent core, and is usually not more than, for example, about 10% above the caliper of the core. The absorbent article can be made to a greater caliper, by for example incorporating additional absorbent fibrous, for example tissue, or other material on one or both sides of the core, but unless the material is selected carefully this may detract from the performance of the absorbent core.

It is a particular advantage of the invention that the diaper or other article can be thin and compact and yet can have good absorption properties. The thin compact nature is beneficial for manufacturing and packaging reasons and is convenient to the user.

Figure 1B:
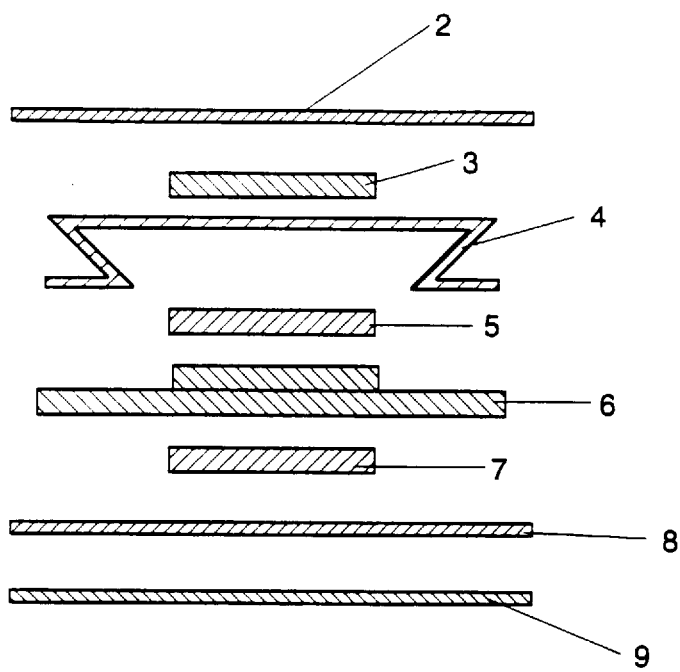
FIG. 1b is a diagrammatic cross-sectional view showing the layer structure of the article in the cross direction.
Figure 1C:
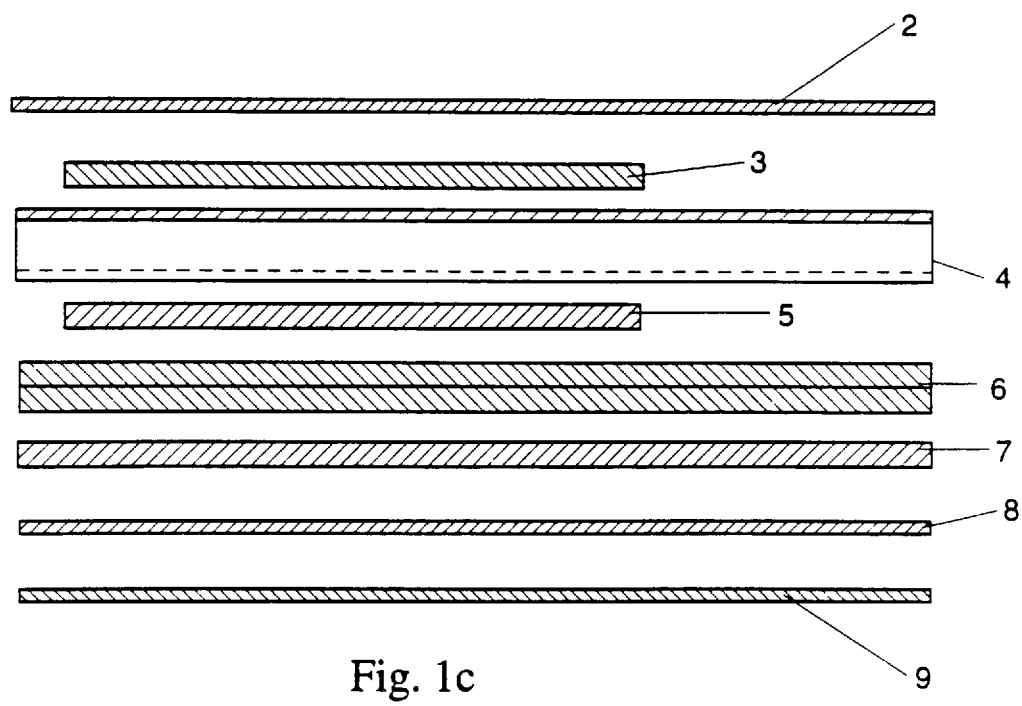
FIG. 1c is a diagrammatic cross-section of the article in the length direction.

Referring to the dimensions on FIGS. 1a to 1c, in a typical diaper for a baby in the weight range 9–18 kg width c is about 7.6 cm (3"), width d is about 10.2 cm (4"), length e is about 25.5 cm (10"), and length f is about 40 cm (15.7").

Although the various layers of the absorbent body may be co-extensive, it is often convenient for the upper assembly to cover only those parts of the storage assembly that can be expected to receive the highest initial load of urine, menstrual fluid or other body discharge. Thus the upper assembly may be in the front half or two thirds of the diaper.

Additional Embodiments of the Invention

Although the use of superabsorbent bodies and articles wherein the first superabsorbent material has the GLP values defined above is very valuable, other valuable absorbent bodies are those which comprise in sequence from the top, an upper assembly comprising an acquisition layer, the upper assembly also comprising a first superabsorbent material having a substantially non-decreasing Dynamic Swelling Rate (generally as a separate layer beneath the acquisition layer), and a lower assembly comprising a second capillary material and a second superabsorbent material having a Dynamic Swelling Rate of at least 0.2 g/g/s and an Absorption Against Pressure of at least 15 g/g, and preferably at least 20 g/g, at 50 g/cm$^2$, wherein the Dynamic Swelling Rate of the second superabsorbent material is at least 1.5 times the Dynamic Swelling Rate of the second superabsorbent material.

The upper assembly may comprise an upper acquisition layer which may be a fibrous, foam or other porous or capillary material but is preferably a first fibrous material, all as described above. Preferably it has a wet compressibility as described above.

The second capillary material may be foam or other porous or capillary material but is preferably a second fibrous material. Preferably the first structure comprises in sequence the upper acquisition layer having the defined wet compressibility and drip capacity formed of first material and a layer comprising the first superabsorbent material, and the lower assembly preferably comprises in sequence an upper layer of second fibrous, foam or other capillary material and a lower layer comprising the second superabsorbent material. The general construction and properties of the layers, except for the particular superabsorbent materials, may all be as described above.

Even when the first superabsorbent material has a GLP that is relatively low, this construction can give beneficial results because of the difference of rates of absorption of the first and second superabsorbence, coupled with the substantially non-decreasing Dynamic Swelling Rate for the first superabsorbent.

Test Methods

All tests are carried out at about 23±2° C. and at 50±10% relative humidity.

The specific synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of $Na_2SO_4$; 0.85 g/l of $(NH_4)H_2PO_4$; 0.15 g/l $(NH_4)H_2PO_4$; 0.19 g/l of $CaCl_2$; ad 0.23 g/l of $MgCl_2$. All of the chemicals are of reagent grade. The pH of the synthetic Urine is in the range of 6.0 to 6.4.

Sample Pad Preparation for Wet Compressibility and Drip Capacity Tests

The sample pads are prepared using a padmaker machine, such as is described below or an equivalent machine, which provides a consistent and homogeneous laydown of fluff.

Figure 3:
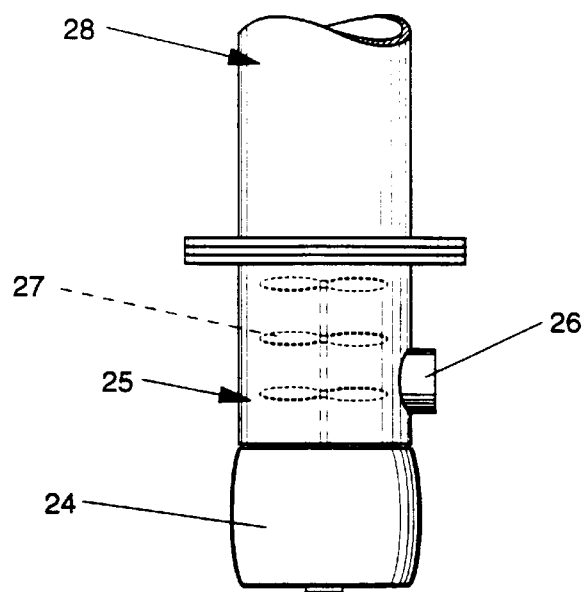
FIG. 3 is an enlarged view of a portion of FIG. 2.
Figure 2:
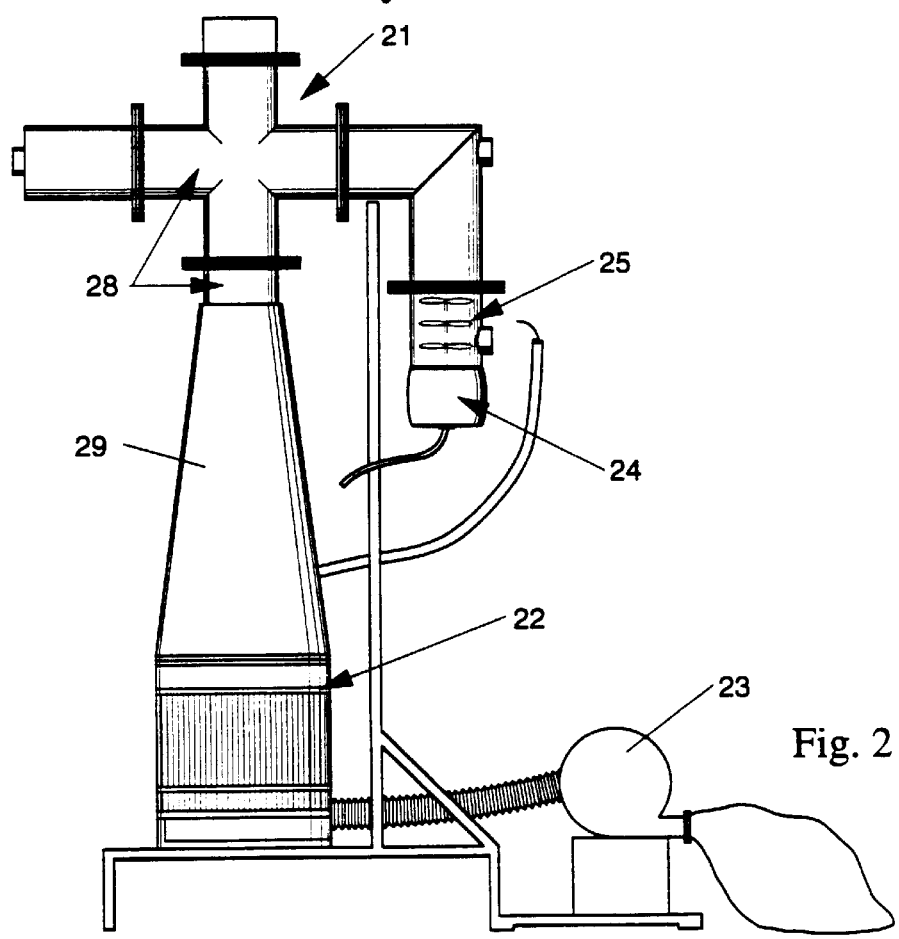
FIG. 2 is a side view of an air laid felt padmaker machine used to make the sample pads for the Wet Compressibility and Drip Capacity Tests.

Four 30 g portions of dry fluff (or equivalent material, for example chemically cross-linked cellulose) are weighed out. A ply of tissue porous enough for air to pass through it while retaining fluff on it, is cut to 36.8 cm×36.8 cm (14.5"×14.5"), and is placed evenly on the forming screen (22) of an air laid felt padmaker machine shown in FIGS. 2 and 3 21. The tissue (not shown) completely covers the forming screen and is made to curve up at its sides to prevent escape of the fluff. The tissue forms the bottom of the pad.

The vacuum 22, chamber motor 24 and compressed air supply on the padmaker machine are turned on. One 30 g portion of fluff is added to the sample chamber 25 on the padmaker machine in small amounts via the sample feed 26 and without obstructing the blades 27 of the machine. Compressed air is circulated vigorously in the chamber to expedite separation and passage of the fibres through the plexiglass cylinder 28 and the prismoid column 29 to the forming screen 22.

The vacuum 23 is turned off and the forming screen 22 is pulled out of the padmaker machine 21 and rotated through a quarter turn in the clockwise direction. The screen is returned to the padmaker machine. Another 30 g portion of fluff is added to the chamber 25 on the machine and the above procedure is repeated. Fluff is added in the same manner until all four portions have been transferred to the forming screen. The forming screen, and the pad formed thereon, is then removed from the padmaker machine, and the pad is carefully transferred from the screen to a piece of cardboard, or similar smooth flat surface. A second ply of tissue is added to the top of the pad, and a second piece of cardboard placed on top of that.

A steel weight having dimensions of around 35.6 cm×35.6 cm×2.5 cm (14"×14"×1") having a weight of around 16.3 kg (36 lbs) is placed on top of the pad for approximately 120 seconds, or longer until the pad is needed. The weight is then removed and the pad is pressed by application of a force of around 4,500 kg (10,000 lbs) on a large Carver press to improve pad integrity. The pad is removed from the press and trimmed on a paper cutter to have dimensions around 30.5 cm×30.5 cm (12"×12"), and is then further cut according to the size required by the particular test in which it is to be used.

The use of a padmaker machine to form the sample pads is not intended to be limiting. Any suitable method can be used provided a consistent and homogeneous laydown of fluff is achieved, which is then compressed under the above conditions to give a pad having substantially the same density and basis weight as achieved above.

Wet Compressibility Test

This test is designed to measure the volume of a pad of fibrous material under varying load conditions when wet. The objective is to measure the fibrous material's resistance to load by measuring the volume maintained under that load.

A fluff test pad is prepared as described above. Any tissue present on the surfaces of the pad is removed. The pad is then densified under a 3.6 kg cm$^{-2}$ (51 psi) load for pad integrity reasons using a Carver laboratory press. The thickness of the pad is measured and its fibre density calculated by pad weight÷(pad thickness×pad area).

The dry weight of the pad is multiplied by 10, and this represents the target wet weight on loading. The dry pad is transferred onto a top loading balance having a 0.01 g sensitivity. Synthetic urine is dispensed slowly onto the pad until the target wet weight is achieved as measured by the balance. The wet pad is carefully transferred onto the surface of a compressibility tester of the Buckeye design, and a weight having substantially the same area as the pad (about 10.2 cm×10.2 cm) and corresponding to a pressure of 77 g cm$^{-2}$ (1.1 psi) is lowered slowly onto the pad. The pad is left for 60 seconds to allow it to equilibrate under the load, and then the thickness of the compressed pad is recorded using calipers.

The Wet Compressibility is the void volume per gram of dry fluff and is calculated as follows:

Void Volume (cm$^3$)=Total Volume−Fibre Volume=(pad thickness under load (cm)×pad area (cm$^2$))−(pad dry weight (g)/fibre density (g cm$^3$)

Wet Compressibility=Void volume per gram=[(pad thickness underload (cm)×pad area (cm$^2$))−(pad dry wt. (g)/fibre density (g cm$^{-3}$)]÷pad dry wt. (g)

where fibre density is calculated from the initial pad weight and thickness measurements (i.e. under no load conditions).

Drip Capacity Test

A sample pad prepared as described above is cut on a paper cutter to have dimensions 7.5 cm×7.5 cm. The pad is weighed and is placed on a large mesh wire screen which is in turn positioned on a drip tray. The whole apparatus is then mounted on a top-loading balance.

Synthetic urine is introduced via a pump (Model 7520-00, as supplied by Cole-Parmer Instruments Company, Chicago, USA) into the centre of the sample pad at a rate of 5±0.25 ml s$^{-1}$. The time for the pad to release the first drop of synthetic urine through the bottom of the pad and into the drip tray is recorded. The pump is immediately stopped as soon as this occurs. The time recorded and the pumping rate are then used to calculate the volume (ml) of synthetic urine absorbed by the sample on reaching saturation, i.e. when the sample starts to drip. The balance can be used to check this periodically, thereby minimising any variation in the pump delivering the synthetic urine. This is known as the Drip Capacity, and is given as the ratio:

Urine Retained By Sample Pad on Saturation (ml)

Dry Weight of sample (g)

Dynamic Swelling Rate Test 0.358 g, to the nearest 0.001 g, of dry superabsorbent material is placed in a standard test tube having an outer diameter of 16 mm, a height of 125 mm and a wall thickness of 0.8 mm, which is supported to be vertical, for example by placing in a test tube stand. (Only previously unused test tubes should be used in this test, and should be discarded after use).

10 ml Jayco synthetic urine is added to the test tube using an automatic pipette at a rate of about 5 ml s$^{-1}$. As the synthetic urine is added the superabsorbent material begins to swell, forming a front that moves upwards in the test tube. The height of the front is recorded as a function of time, either manually or using an image analyser after video recording. The height of the front is then translated into momentary X-load, X(t)-load, of synthetic urine per gram dry superabsorbent material, wherein X(t)=h(t)×28/H, where h(t) is the length of the swollen superabsorbent material up the test tube at time t, and H is the total height of synthetic urine in the tube that would correspond to a total X-load of 28 (10 g synthetic urine absorbed by 0.358 g superabsorbent gives a X-load of 28); the X-load being the weight in grams of synthetic urine that 1 gram of dry of superabsorbent material can absorb.

The X(t)-load is then plotted against time. It is assumed that the equilibrium absorbent capacity of the superabsorbent material under test is greater than 28 g g$^{-1}$.

The ratio of the X(t)-load to the time t at which it is measured is called the "Swelling Rate Function" (SR), and is the average swelling rate in achieving X(t), i.e.

$$SR(t) = \frac{X(t)}{t}.$$

The "Dynamic Swelling Rate" (DSR) is the value of the swelling rate function when X(t) is 28 gg$^{-1}$, i.e.

$$DSR = \frac{28 g g^{-1}}{t_{28}},$$

where $t_{28}$ is the time to reach $X(t)=28$ g g$^{-1}$.

If no gel blocking occurs at the front of the superabsorbent material the material can be said to be relatively permeable and the graph of X(t) against time will be a substantially horizontal line. This means that the function SR(t) is substantially constant.

Alternatively, with some materials permeability increases during swelling, in which case SR(t) increases with increasing time, also showing the absence of gel blocking. If gel blocking occurs, however, permeability decreases during swelling SR(t) decreases with increasing time.

In the context of this application a superabsorbent material is said to have a substantially non-decreasing dynamic swelling rate if the swelling rate function does not decrease substantially between the two times $t_{14}$ (the time when the superabsorbent material is swollen to 50%, i.e. where $X(t) = 14$ g g$^{-1}$) and $t_{28}$, as defined above. That means the relative deviation $[SR(t_{14})-SR(t_{28})] \div SR(t_{28})$ of the swelling rates at $t_{14}$ and $t_{28}$ is less than 50%, preferably less than 25%, more preferably less than 10% or most preferably less than or equal to 0%.

Absorption Against Pressure Test

This test measures the absorptive capacity of a superabsorbent material absorbing against an external pressure of 20 g cm$^{-2}$ (0.3 psi), in terms of the uniaxial swelling of the superabsorbent material against that pressure.

A ceramic filter plate having a diameter of 120 mm and 0 porosity (ceramic filter Duran from Schott) is placed in a petridish having a diameter of 150 mm and a height of 30 mm. 0.9% by weight sodium chloride solution in distilled water is added to the Petri dish so that the filter plate is covered. A round filter paper having a diameter of 125 mm (Schwarzband 589 from Schleicher and Schull) is placed on the filter plate and is thoroughly wetted with the sodium chloride solution.

A Plexiglass cylinder having an inner diameter of 60 mm +/−0.1 mm and a height of 50 mm, is closed at its bottom with a screen filter cloth having apertures of a diameter of 36 μm (400 mesh). 0.9000 g+/−0.0005 g of superabsorbent material is carefully scattered onto the filter screen of a clean and dry Plexiglass cylinder, as described. It is necessary to obtain a homogeneous distribution of superabsorbent material on the mesh.

A cover plate having an outer diameter of 59 mm+/−0.1 mm, an inner diameter of 51 mm and the height of 25 mm, having an attached weight having a diameter of 50 mm and a height of 34 mm, has a total weight of 565 g, which correspond to a pressure of 20 gcm$^{-2}$ (0.3 psi). The cover plate and weights are placed in the cylinder and the complete cylinder apparatus is weighed on a balance to the nearest 0.01 g. The complete cylinder apparatus is then placed on the wetted filter paper in the Petri dish, and is allowed to absorb for 1 hour. The cylinder apparatus is then removed from the filter plate and is re-weighed.

The cylinder apparatus and filter plate should be cleaned thoroughly between measurements, and the sodium chloride solution and filter paper should be renewed after each measurement.

The absorption against pressure (AAP is calculated as follows:

AAP=[(weight of cylinder apparatus after absorption)−(weight of cylinder apparatus when dry)]÷(initial weight of superabsorbent material).

When the value is to be measured at 50 g/cm$^2$ (0.7 psi) the weight is correspondingly increased.

Performance Under Pressure (PUP) Test

The PUP test determines the following Performance Under Pressure parameters for an AGM that is laterally confined in a piston/cylinder apparatus under a high confining pressure:

1. Maximum Absorption/Transport Rate (inunits of gm/cm$^2$/sec$^{0.5}$)
2. Capacity (in units of gm/gm; at specified times)

The objective of the test is to assess the impact of in-use pressure on demand absorption and fluid transport by an AGM layer, where an AGM is used at high concentrations in a diaper.

The test fluid for the PUP test is Jayco synthetic urine. This fluid is absorbed by the AGM under demand absorption conditions at near-zero hydrostatic pressure.

A piston/cylinder apparatus is used to laterally confine the AGM and impose a specified static confining pressure. The bottom of the cylinder is faced with a No. 400 mesh screen to retain dry/swollen AGM and permit absorption and z-direction transport of urine. A computer-interfaced sorption apparatus is used to measure urine absorption versus time.

A piston/cylinder apparatus is used for this measurement. The cylinder is bored from a transparent Lexan rod (or equivalent) and has a inner diameter of 6.00 cm (area=28.27 cm), with a wall thickness of approximately 5 mm and a height of appromiately 5 cm. The bottom of the cylinder is faced with a No. 400 mesh stainless-steel screen cloth that is biaxially stretched to tautness prior to attachment. The piston consists of a Teflon "cup" and a stainless steel weight. The Teflon cup is machined to fit into the cylinder within tight tolerances. The cylindrical stainless steel weight is machined to fit snugly within the cup and fitted with a handle on the top. The combined weight of the Teflon cup and stainless steel weight is 1390 gm, which corresponds to 0.70 psi for an area of 28.27 cm$^2$.

The components of this apparatus are sized such that the flow rate of synthetic urine through the apparatus under a 10 cm hydrostatic head is at least 0.01 gm/cm$^2$/sec, where the flow rate is normalised by the area of the fritted disc in the apparatus. Factors particularly impactful on system permeability are the permeability of the fritted disc and the inner diameters of glass tubing and stopcocks.

The apparatus' reservoir is positioned on an analytical balance that is accurate to 0.01 gm with a drift of less than 0.1 gm/hr. A more accurate/stable balance is preferred. The balance is preferably interfaced to a computer with software than can (i) monitor balance weight change at pre-set time intervals from the initiation of the PUP test and (ii) be set to auto initiate on a weight change of 0.01–0.05 gm, depending on balance sensitivity. The dip tube entering the reservoir should not contact either the bottom of the reservoir or its cover. The volume of fluid in the reservoir should be sufficient such that at least 40 ml can be extracted during the experiment without drawing in air. The fluid level in the reservoir, at the initiation of the experiment, should be −2 mm below the top surface of the fritted disc. This can be confirmed by placing a small drop of fluid on the disc and gravimetrically monitoring its slow flow back into the reservoir. This level should not change significantly when the piston/cylinder apparatus is positioned on the frit. The reservoir should have a sufficiently large diameter (e.g. ~14 cm) so that withdrawal of ~40 ml results in only a small change in the fluid height (e.g. <3 mm).

Jayco synthetic urine is prepared by dissolving a mixture of 2.0 gm KCl, 2.0 gm Na$_2$SO$_4$, 0.85 gm NH$_4$H$_2$PO$_4$, 0.15 gm $(NH_4)_2HPO_4$, 0.19 gm $CaCl_2$, and 0.23 gm $MgCl_2$ to 1.0 liters with distilled water. The salt mixture can by purchased from Endovations, Reading, Pa. (cat no. JA-00131-000-01).

Prior to measurement, the apparatus is filled with synthetic urine. The fritted disc is forward flushed with urine so that it is filled with fresh solution. To the extent possible, air bubbles are removed from the bottom surface of the frit and all tubing that connects the frit to the reservoir. The following procedures are carried out by sequential operation of the 3-way valves:

1. Excess fluid is removed (e.g. poured) from the fritted funnel.
2. The solution height/weight of the reservoir is adjusted to the proper level/value.
3. The frit is positioned at the correct height relative to the reservoir.
4. The funnel is covered.
5. The reservoir and frit are equilibrated with connecting valves open.
6. All valves are closed.
7. The 3-way valve connecting the fritted funnel to the drain is positioned so that the funnel is open to the drain tube.
8. The system is allowed to equilibrate in this position for 5 minutes.
9. The 3-way valve is returned to its closed position.

Steps Nos. 7–9 temporarily "dries" the surface of the frit by exposing it to a small hydrostatic suction. Typically ~0.2 gm of fluid is drained from the system during this procedure. This procedure prevents premature absorption when the piston/cylinder is positioned on the frit. The quantity of fluid that drains from the frit in this procedure (called the frit correction weight) is measured by conducting the PUP experiment (see below) for a time period of 15 minutes without the piston/cylinder apparatus. Essentially all of the fluid drained from the frit via this procedure is very quickly reabsorbed by the frit when the experiment is initiated. Thus, it is necessary to substract this frit-correction weight from weights of fluid removed from the reservoir during the PUP test (see below).

0.9 gm of AGM (corresponding to a basis weight of 0.032 gm/cm$^2$) is added to the cylinder and spread evenly n the screen via gently shaking and/or tapping cylinder. For most AGMs, moisture content is typically less than 5%. For these AGMs, the added AGM weight can be determined on a wet-weight (as it is) basis. For AGMs having a moisture content greater than about 5%, the added AGM weight should be corrected for moisture (i.e. the added AGM should be 0.9 gm on a dry-weight basis). Care is taken to prevent AGM from adhering to the cylinder walls. The Teflon insert is slid into the cylinder and positioned on top of the AGM. The insert can be turned gently to help distribute the AGM. The piston/cylinder is placed on top of the frit, the appropriate stainless steel weight is slipped into the Teflon insert, and the funnel is covered. After the balance reading is checked for stability, the experiment is initiated by opening the valves between frit and reservoir. With auto initiation, data collection commences immediately, as the fritted disc begins to reabsorb fluid. Data is recorded for a time period of at least 60 minutes. Readings should be more frequent at early times(e.g. 0–10 min), when fluid is being absorbed rapidly. Recording data for times longer than 60 minutes, although not required often reveals interesting phenomena as the AGM approaches equilibrium.

Moisture content of the AGM is determined separately using the standard P&G method (% weight loss after 3 hr @ 105C). All values for gm/gm capacities are reported on an AGM dry-weight basis.

PUP Capacity is reported in units of gm/gm. PUP Capacity at any time is determined as follows:

$$\text{PUP Capacity}(t) = [W_r(t=0) - W_r(t) - W_{fc}]/\{W_{AGM;drybasis}\}$$

where t is the elapsed time from initiation, $W_r(t=0)$ is the weight in grams of the reservoir prior to initiation, $W_r(t)$ is the weight in grams of the reservoir at elapsed time t, $W_{fc}$ is the frit correction weight in grams (measured separately), and $W_{AGM;dry\ basis}$ is the dry weight in grams of the AGM. PUP Capacity is reported for times of 5, 10 30 and 60 minutes after initiation.

The PUP Absorption/Transport Rate is reported in units of gm/cm$^2$/sec$^{0.5}$. The PUP Rate at any time is determined as follows:

$$\text{PUP Absorption/Transport Rate}(t) = (1/A_c) \times [W_r(t) - W_r(t+dt)]/[(t+dt)^{0.5} - t^{0.5}]$$

where t is elapsed time in units of seconds, $W_r(t)$ is the weight in grams of the reservoir at elapsed time t, $W_r(t+\delta t)$ is the weight in grams of the reservoir at elapsed time t+δt, and $A_c$ is the area of the cylinder in units of cm$^2$. If determined graphically the PUP Uptake Rate is the tangent to the uptake curve where the y-axis is fluid uptake in units of gm/cm$^2$ and the x-axis is the square root of time, where time is in units of seconds. Whether determined numerically or graphically, the rate at any uptake/time is preferably determined after "smoothing" the output data.

The PUP Absorption/Transport rate typically starts off at or near its maximum value, remains relatively constant for a sustained period of uptake/time, and then decreases as the maximum capacity is approached. Only the "Maximum PUP Absorption/Transport Rate" is reported. This maximum rate typically occurs early in the absorption process. However, for some AGMs there may be either a lag time due to slow wetting of dry particles or a very-fast initial rate due to very-rapid wetting of dry particles. In order to minimise the impact of both these effects and insure that the reported maximum PUP rate reflects transport through a sufficiently thick layer of swollen AGM, only values of Absorption/Transport Rate occurring after the uptake of ~0.14 gm/cm$^2$ (~4 gm of fluid) are considered in the determination of the maximum rate.

Sieve Test

The particle size distribution of superabsorbent material is determined by placing a known weight of a sample in a Retsch mechanical sieving device, and shaking for a specified period of time under defined conditions. Sample sections is retained on each sieve and the bottom pan are weighed and reported as percentages of the original sample weight.

100 g+/−0.5 g of dry superabsorbent polymeric material is weighed into a sample cup which is then closed by a lid.

Four sieves are nested from bottom to top as follows: stainless steel bottom pan, No. 325, No. 100, No. 50 and No. 20; these being numbers of the U.S. sieve series (ASTM-E-11-61). The sample is transferred to the upper most of the series of sieves, and the powder is distributed evenly around the screen. A stainless steel cover is placed on the No. 20 sieve.

The nested sieves are placed in position on a Retsch testing sieve shaker Vibotronic Type VE1 with timer. It is ensured that the Retsch lid fits as tightly as possible against the top of the shaker. The timer is set for 10 minutes, and started to begin the test. When the shaker has stopped, the nest of sieves is removed from the shaker.

Each of the sieve fractions retained by the sieve is then weighed, for example by different measurements, to the nearest 0.1.

It is important to work quickly in this test to avoid moisture pickup by the superabsorbent material.

The median mass particle size is determined by plotting the cumulative particle size distribution curve (i.e. mass-% of material not passing through the mesh openings vs. diameter of the sieve mesh opening) and by interpolating the sieve opening which corresponds to 50% of the cumulative distribution.

Teabag Retention Capacity Test

The superabsorbent material is placed within a "teabag", immersed in a synthetic urine solution for 20 minutes, and then centrifuged for 3 minutes. The ratio of the retained liquid weight to the initial weight of the dry superabsorbent material is the absorptive capacity of the superabsorbent material.

21 of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from a company called Teekanne in Dusseldorf, Germany. The pouch is heat sealable with a standard kitchen plastic bag sealing device (e.g. VACUPACK$_2$ PLUS from Krups, Germany).

The teabag is opened by carefully cutting it partially, and is then weighed. A 0.200 g+/−0.005 g sample of the superabsorbent material is placed in the teabag. The teabag is then closed with a heat sealer. This is called the sample teabag.

An empty teabag is sealed and used as a blank.

Each teabag is then held horizontally, and the sample teabag is shaken so as to distribute the superabsorbent material evenly throughout the bag. The sample teabag and the blank teabag are then laid on the surface of the synthetic urine, and submerged for about 5 seconds using a spatular to allow complete wetting (the teabags will float on the surface of the synthetic urine but are completely wetted). The timer is started immediately.

After 20 minutes soaking time the sample teabag and the blank teabag are removed from the synthetic urine, and placed in a Bauknecht WS130, Bosch 772 NZK096 or equivalent centrifuge (230 mm diameter), so that each bag sticks to the outer wall of the centrifuge basket. [This can be arranged, for example, by folding an end of the teabag in the direction of the centrifuge spin to absorb the initial force?] The centrifuge lid is closed, the centrifuge is started, and the speed increased quickly to 1,400 rpm. Once the centrifuge has been stabilised at 1,400 rpm the timer is started. After 3 minutes, the centrifuge is stopped.

The sample teabag and the blank teabag are removed and weighed separately.

The absorptive capacity (AC) for the sample of superabsorbent hydrogel-forming material is calculated as follows:

AC=[(sample teabag weight after centrifuging)−(blank teabag weight after centrifuging)÷(dry superabsorbent hydrogel-forming material weight)]÷(dry superabsorbent material weight).

Stack Height Test

The stack height is designed to test the packaging potential of a stack of 10 absorbent articles, e.g. diapers, to simulate in-pack conditions.

Ten absorbent articles, or absorbent cores according to this invention assembled into a chassis including a topsheet (as described above) and a backsheet (as described above) to simulate a finished product deliverable to the market, are typically folded at the centre (doubled over) to conform to package width and length dimensions. The stack of 10 articles is precompressed in a hydraulic press (Thwing-Albert Instrument. Company, Model TA 240-10, Alpha Hydraulic Press/Sample Cutter, Philadelphia, U.S.A.) under a load of 800 kg for 3 seconds. The precompressed structures are then placed in an Instron Series 6000 tension-compression testing device, available from Instron Ltd. (Bucks, U.K.), and a compression curve is recorded. The compression curve plots the stack height, or caliper of the sample stack, as a function of the exerted compression force. The force is readily converted to determine the pressure required to achieve a given caliper.

The "stack height" is the height or caliper (under a given pressure) of a single article and is determined by averaging the height measured in the stack height test by the number of articles in the stack.

Acquisition Rate Test

Figure 4:
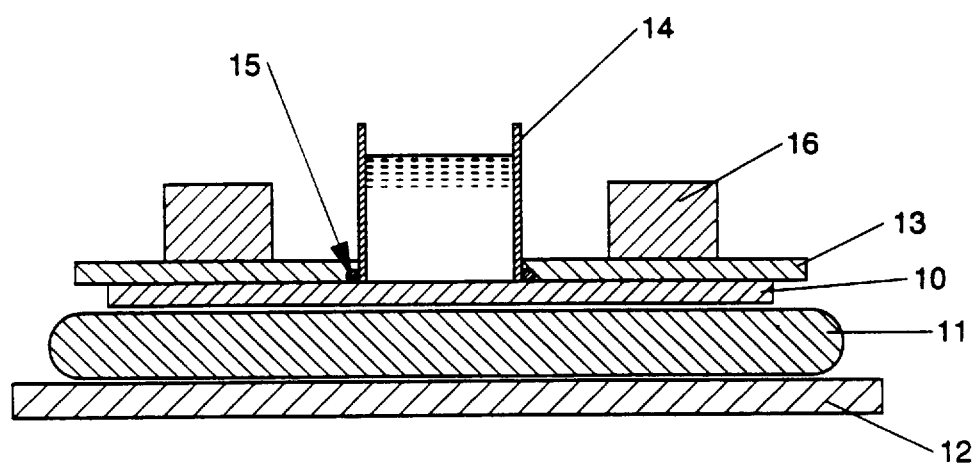
FIG. 4 is a cross-sectional view of the apparatus used in the Fluid Acquisition Test.

Referring to FIG. 4, an absorbent structure (10) is loaded with a 50 ml gush of synthetic urine at a rate of 10 ml s$^{-1}$ using a pump (Model 7520-00, supplied by Cole Parmer Instruments Co., Chicago, U.S.A.), from a height of 5 cm above the sample surface. The time to absorb the urine is recorded by a timer. The gush is repeated every 5 minutes at precisely 5 minute gush intervals until the theoretical capacity is reached.

The test sample, which comprises a core and includes a topsheet (as described above) and a backsheet (as described above), is arranged to lie flat on a foam platform 11 within a perspex box (only the base 12 of which is shown). A perspex plate 13 having a 5 cm diameter opening substantially in its middle is placed on top of the sample. Synthetic urine is introduced to the sample through a cylinder 14 fitted and glued into the opening. Electrodes 15 are located on the lowest surface of the plate, in contact with the surface of the absorbent structure 10. The electrodes are connected to the timer. Loads 16 are placed on top of the plate to simulate, for example a baby's weight. A pressure of 50 g cm$^{-2}$ (0.7 psi) is typically utilised in this test.

As urine is introduced into the cylinder it typically builds up on top of the absorbent structure thereby completing an electrical circuit between the electrodes. This starts the timer. The timer is stopped when the absorbent structure has absorbed the gush of urine, and the electrical contact between the electrodes is broken.

The acquisition rate is defined as the gush volume absorbed (ml) per unit time (s). The acquisition rate is calculated for each gush introduced into the sample.

As mentioned above, it is considered beneficial in respect of the absorbent core of the invention to determine the acquisition rate on loading to 50% of the theoretical capacity. To determine this point one can either plot the acquisition rate as a function of the total volume of synthetic urine added, and then determine the acquisition rate on absorption to 50% of the theoretical capacity. Alternatively, one can determine it directly by taking the acquisition rate for the nearest gush if this lies within 15 ml of the middle value.

X,Y-Demand Absorbency Test

The X,Y-demand absorbency test method consists of a version of a standard demand wettability test. For reference, standard demand absorbency tests are described in Chatterjee, P. K. (Ed.) Absorbency, Chapter II, pp. 60–62, Elsevier Science Publisher B.V., Amsterdam, The Netherlands (1985).

The apparatus used to conduct this test is shown in FIGS. 5 and 6. The apparatus 100 consists of a square sample basket 102 suspended on a frame 104. The inside dimensions of the basket are 10.2 cm×7.6 cm (4"×3"). The height of the basket 102 is adjustable via a gear mechanism 106. A fluid reservoir 108 is placed on an electronic balance 110 connected to a computer 112.

Figure 7:
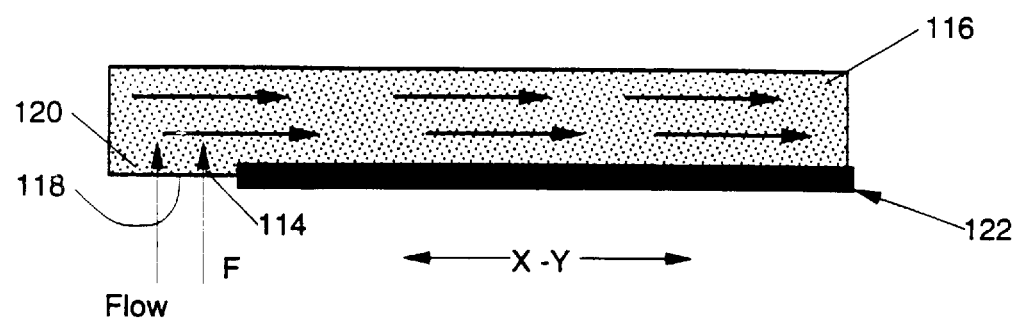
FIG. 7 is a cross-sectional view of liquid flowing in the X-Y plane in an absorbent core according to the invention.

The x-y plane test is shown schematically in FIG. 7. In the x-y plane test, the screen 114 is only present in a 2.54 cm×7.62 cm (1"×3") area 118 along one edge 120 of the sample basket bottom. The remainder of the sample basket bottom, designated 122, is made of Plexiglas and is fluid impervious. The sides of the sample basket that are in contact with the sample are also made of Plexiglas and are fluid impervious. As shown in FIG. 7, this test requires the sample 116, comprising a core and including a topsheet (as described above) and a backsheet (as described above), to first demand the fluid in the z-direction, and then transport it a maximum of 7.62 cm (3") in the horizontal (x-y) plane. The results from the x-y plane test provide a measurement of the sample's ability to distribute fluid under potential in-use conditions. The x-y plane test is carried out with the absorbent structure sample 116 confined under a 20 g cm$^{-2}$ (0.3 psi) load applied evenly to the upper surface of the sample 116.

The test procedure is as follows. First, a 10.2 cm×7.6 cm (4"×3") sample of an absorbent core of the invention is prepared. The fluid reservoir 108 is filled with about 6800 ml of synthetic urine and set on an electronic balance 110 under the test apparatus 100. Then the sample basket 102 is lowered until the fluid level is just at the level near the tope of the wire screen 114. A piece of commercial available 2-ply BOUNTY® paper towel 124 is placed on the wire screen 114 in the bottom of the basket 102. The BOUNTY® towel 124 ensures that consistent fluid contact with the underside of the core sample 116 is maintained throughout the duration of the test.

The applied weight 126 is attached to a square metal plate 128 with dimensions slightly smaller than the inner dimensions of the sample basket 102. Then the top side of the core sample 116 is attached to the bottom of the above-mentioned plate 128 via double sided tape 130, or spray adhesive. At time=zero, the sample 116 is placed into the sample basket 102.

The test is run over a duration of 2000 seconds. At 2000 seconds the final X-Y load, $X_{end}$, is determined by balance measurement (corrected for any evaporation loss over this period)÷dry weight of sample. From $X_{end}$ the X-Y load at 90% of this value, $X_{90}$, is calculated, and the corresponding time, $t_{90}$, determined. The fluid uptake rate is defined as the ratio $X_{90}/t_{90}$.

Absorptive Capacity of Fibrous Material by the X,Y-Demand Absorbency Test

The test is carried out identical to that described above except that the sample consists of fibrous material only. In this instance the fibre capacity is $X_{end}$ as opposed to $X_{90}$.

Rewet Test

This test is particularly important with regard to determining the in-use performance of an absorbent core, or an absorbent article in which such a core is incorporated. The test is based upon the measurement of the wetting of a stack of filter papers placed on top of an absorbent core that is loaded with synthetic urine and then placed under a load.

An absorbent core including a topsheet (as described above) and a backsheet (as described above) is laid out flat on a smooth surface with the topsheet uppermost. A volume of synthetic urine equal to 75% of the Theoretical Basis Capacity, calculated as described above, is added at a rate of 7 ml s$^{-1}$ to the absorbent core at a loading point centrally located with regard to the width of the core and approximately 11 cm from the front core edge.

A weight having dimensions 10.2 cm×10.2 cm corresponding to a load of 50 g cm$^{-2}$ (0.7 psi) is placed centrally over the loading point and the core is allowed to equilibrate for 15 minutes under this load. The weight is then removed and 5 layers of pre-weighed filter paper (Eaton Dikeman 939, Nr 7) having dimensions of 10.2 cm×10.2 cm are placed rough side down centrally over the loading point, and the weight is reapplied for 30 seconds. The weight is then removed and the filter papers are weighed. The difference in filter paper weight is the first rewet value.

Five new pre-weighed filter papers are then placed on the absorbent core in a similar manner, and the weight is placed on top of them for 30 seconds as before. The weight is removed and the second batch of filter papers are weighed. The difference in filter paper weight is the second rewet value.

The procedure is repeated one more time to determine the third rewet value.

The total rewet is the sum of the three individual rewet values, i.e.:

Total rewet=first rewet+second rewet+third rewet.

Gel Layer Permeability Test

The GLP value is alternatively known as the Saline Flow Conductivity value.

Figure 8:
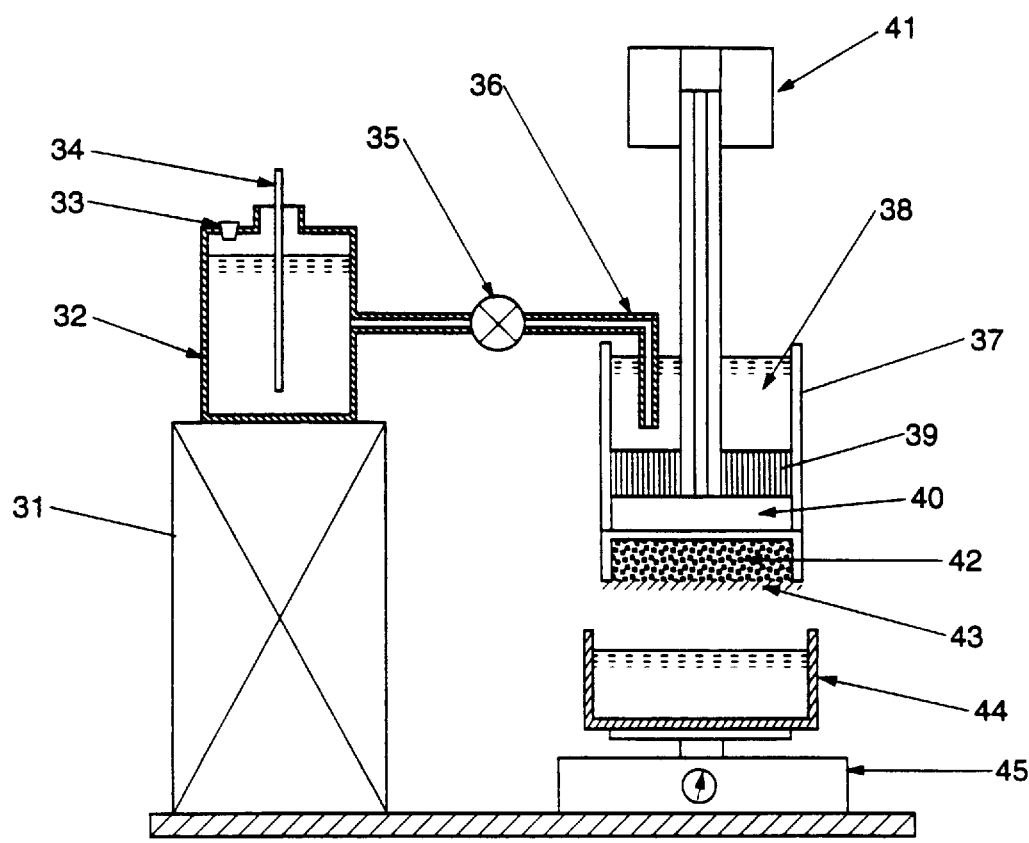
FIG. 8 is a side view of the apparatus used in the Gel Layer Permeability test.

Suitable apparatus for this test is shown in FIG. 8 wherein 31 is a laboratory jack, 32 is a constant hydrostatic head reservoir, 33 is a vent with removable cap, 34 is a tube, 35 is a stop cock in a delivery tube 36 leading to a cylinder 37. This cylinder contains the test fluid 38 and includes a porous piston 39 of Teflon (registered trade mark) having many small holes with the bottom 40 formed of coarse glass frit. The piston is weighted by a weight 41. The sample of particulate superabsorbent material is shown at 42, supported on a 400 mesh screen 43. There is a collection reservoir 44 on a laboratory balance 45.

In particular apparatus that is used in the procedure described below, the cylinder is bored from a transparent Lexan rod or equivalent and has an inner diameter of 6.00 cm (ara=28.27 cm$^2$), a wall thickness of approximately 0.5 cm, and a height of approximately 6.0 cm. The bottom of the cylinder is faced with a No. 400 mesh stainless steel screen cloth that is biaxially stretched to tautness prior to attachment. The piston consists of a fritted glass disc, perforated Teflon piston head, hollow Lexan piston rod, and annular stainless steel weight(s) or their equivalent. The perforated piston head is machined from a solid Teflon rod. It has a height of 0.625 inches and a diameter that is slightly less than that of the cylinder, so that if fits within the cylinder with minimum wall clearances, but still slides freely. The bottom of the piston head contains an approximately 56 mm diameter by 4 mm depth cavity, desinged to accept the fritted glass disc. The centre of the piston head has a threaded 0.625 inch opening (18 threads/inch) for the piston rod. Between the piston rod opening and the circumference of the piston head are four circumferentially arranged rings of holes, with 24 holes per ring. The holes in each ring are spaced by approximately 15 degrees and offset by approximately 7.5 degrees from the holes in adjacent rings. Hole diameters range from 0.111 inch in the inner row to 0.204 inch in the outer row. The holes pass vertically through the piston head, allowing fluid to directly access the fritted disc. The fritted glass disc is chosen for high permeability (e.g. Chemglass Cat No. CG-201-40, 60 mm diameter; X-Coarse Porosity) and is ground so that it fits snugly in the piston head, with the bottom of the disc flush with the bottom of the cylinder head. The hollow piston rod is machined from a Lexan rod. It has a outer diameter of 0.875 inches and an inner diameter of 0.250 inches. The bottom approximately 0.5 inches is threaded to match the opening in the piston head. The top 1.0 inch is 0.623 inches in diameter, forming a collar to support the stainless steel weight(s). Fluid passing through the rod can directly access the fritted disc. The annular stainless steel weight(s) have an inner diameter of 0.625 inches, so that they slip onto the piston rod and rest on the collar. The combined weight of the fritted glass disc, piston head, piston rod and stainless steel weights equals 596 gms, which corresponds to 0.30 psi for an area of 28.27 $cm^2$. The cylinder cover is machined from Lexan or equivalent and is dimensioned to cover the cylinder. It has an 0.877 inch opening in the centre for vertically aligning the piston rod and a second opening near the edge for introducing fluid into the cylinder.

The assembly that is used for measuring permeability depends on the flow rate of the saline solution through the gel layer. For flow rates greater than about 0.02 gm/sec, a permeability assembly consisting of (i) a ring-supported rigid stainless steel screen (16 mesh or less), for supporting the cylinder in a horizontal position, with an air gap between it and (ii) a container, positioned on an analytical balance, to collect fluid passing through the piston, gel layer, cylinder scree, and support screen, and (iii) a siphon system to maintain the NaCl solution in the cylinder at a constant level or their equivalent can be used. For flow rates less than about 02. gm/sec, it is preferable that there is a continuous fluid path between supply and collection reservoirs. This can be accomplished with the sorption apparatus used for the PUP test method or equivalent, where the cylinder is positioned on the fritted glass disc of the sorption apparatus and a means for maintaining the hydrostatic pressure at approximately 4920 $dyne/cm^2$ is provided.

Jayco synthetic urine is prepared by dissolving a mixture of 2.0 gm KCl, 2.0 gm $Na_2SO_4$, 0.85 gm $NH_4H_2PO_4$, 0.15 gm $(NH_4)_2HPO_4$, 0.19 gm $CaCl_2$, and 0.23 gm $MgCl_2$ to 1.0 liters with distilled water. The salt mixture can be purchased from Endovations, Reading, Pa. (cat No. JA-00131-000-01).

The 0.118M NaCl solution is prepared by dissolving 6.896 gms NaCl (Baker Analysed Reagent or equivalent) to 1.0 liters with distilled water.

An analytical balance accurate to 0.01 gm (e.g. Metler PM400 or equivalent) is typically used to measure the quantity of fluid flowing through the gel layer when the flow rate is about 0.02 gm/sec or greater. A more accurate balance (e.g. Mettler AE200 or equivalent) may be needed for less permeable gel layers having lower flow rates. The balance is preferably interfaced to a computer for monitoring fluid quantity versus time.

The thickness of the gel layer is measured to an accuracy of about 0.1 mm. Any method having the requisite thickness can be used as long, as the weights are not removed and the gel layer is not additionally compressed or disturbed during the measurement. Using a caliper gauge (e.g. Manostat 15-100-500 or equivalent) to measure the gap between the bottom of the stainless steel weight and the top of the cylinder cover, relative to this gap with no AGM in the cylinder is acceptable. Also acceptable is the use of a depth gauge (e.g. Ono Sokki EG-225 or equivalent) to measure the height of the piston above any fixed surface, relative to the height with no AGM in the cylinder.

The experiment is performed at ambient temperature. The following is a description of the method.

0.9 gm aliquot of AGM (corresponding to a basis weight of 0.032 $gm/cm^2$) is added to the cylinder and dispersed evenly on the screen via gently shaking and/or tapping of the cylinder. Considering the potential sensitivity of the flow permeability to particle size, particle size, and size/shape distributions, care should be taken that the aliquot is reasonably representative of the material to be analysed. For most AGMs, moisture content is typically less than 5%. For these, the quantity of AGM to be added can be determined on a wet-weight (as is) basis. For AGMs having a moisture content greater than about 5%, the added AGM weight should be corrected for moisture (i.e. the added AGM should be 0.9 gm on a dry-weight basis). Care is taken to prevent AGM from adhering to the cylinder walls. The piston (minus any weight) is inserted into the cylinder and positioned on top of the dry AGM. If necessary, the piston can be turned gently to more-uniformly distribute the AGM on the cylinder screen. The cylinder is covered with the cylinder cover and the stainless steel weight(s) are positioned on the piston rod.

A fritted disc (coarse or extra coarse), having a diameter greater than that of the cylinder, is positioned in a wide/shallow flat-bottomed container that is filled to the top of the fritted disk with Jayco synthetic urine. The piston/cylinder apparatus is positioned on top of the fritted glass disk. Fluid from the reservoir passes through the fritted disc and is absorbed by the AGM. As the AGM absorbs fluid, a gel layer is formed in the cylinder. After a time period of 60 minutes, the thickness of the gel layer is determined. Care is taken that the gel bed does not lose fluid or take in air during this procedure.

The piston/cylinder apparatus is then transferred to the permeability assembly. If a screen is used to support the cylinder, the screen and any gap between it and the. piston/cylinder apparatus is presaturated with saline solution. If the PUP solution apparatus is used, the surface of the fritted funnel should be minimally elevated relative to the reservoir, with valves between the fritted funnel and reservoir in the open position. (The fritted funnel elevation should be sufficient such that fluid passing through the gel layer does not accumulate in the funnel).

The permeability measurement is initiated by adding NaCl solution through the piston rod in order to expel air from the perforated Teflon disk and then opening up the siphon system (or its equivalent) to fill the cylinder to a height of 5.0 cm above the bottom of the gel layer. Although the experiment is considered to have been initiated ($t_o$) at the time NaCl solution is first added, the time at which a stable hydrostatic pressure, corresponding to 5.0 cm of saline solution and a stable flow rate is attained ($t_s$) is noted. The quantity of fluid passing through the gel layer versus time is determined gravimetrically for a time period of 10 minutes. After the elapsed time, the piston/cylinder apparatus is removed and the thickness of the gel layer is measured. Generally the change in thickness of the gel layer is less than about 10%.

In general, flow rate need not be constant. The time-dependent flow rate through the system, $F_s(t)$ is determined, in units of gm/sec, by dividing the incremental weight of fluid passing through the system (in grams) by incremental time (in seconds). Only data collected for times between $t_s$ and 10 minutes is use for flow rate calculations. Flow rate results between $t_s$ and 10 minutes is used to calculate a value for $F_s(t=0)$, the initial flow rate through the gel layer. $F_s(t=0)$ is calculated by extrapolating the results of a least-squares fit of $F_s(t)$ versus time to $t=0$.

In a separate measurement, the flow rate through the permeability assembly and piston/cylinder apparatus ($F_s$) is measured as described above, except no gel layer is present.

If $F_a$ is much greater than the flow rate through the system when the gel layer is present, $F_s$, then no correction for the flow resistance of the permeability assembly and piston/cylinder apparatus is necessary. In this limit, $F_g=F_s$, where $F_g$ is the contribution of the gel layer to the flow rate of the system. However if this requirement is not satisfied, then the following correction is used to calculate the value of $F_g$ from the values of $F_s$ and $F_a$:

$$F_g=(F_a \times F_s)/(F_a-F_s)$$

The Saline Flow Conductivity K (or the GLP value) of the gel layer is calculated using from $F_g$ using the following equation:

$$K=\{F_g(t=0) \times t_0\}/\{p \times A \times \Delta P\},$$

where $F_g(t=0)$ is the flow rate in gm/sec determined from regression analysis of the flow rate results and any correction due to assembly/apparatus flow resistance, $t_0$ is the thickness of the gel layer in cm, p is the density of the NaCl solution in gm/cm$^3$. A is the area of the gel layer in cm$^2$, $\Delta P$ is the hydrostatic pressure across the gel layer in dyne/cm$^2$, and the saline flow conductivity, K, is in units of cm$^3$ sec/gm.

The average of three determinations should be reported.

For gel layers where the flow rate is substantially constant, a permeability coefficient (k) can be calculated from the saline flow conductivity using the following equation:

$$k=K\eta,$$

where $\eta$ is the viscosity of the NaCl solution in poise and the permeability coefficient, k, is in units of cm$^2$.

The following is a sample calculation:

The measured value of $F_a$ is 250 gm/min=4.2 gm/sec. For a single determination on SX-P (bulk), the extrapolated value for $F_s(t=0)$ is 5.6 gm/min=0.093 gm/sec, with a near-zero slope of 0.09 gm/min$^2$. Correcting for apparatus resistance:

$$F_g=(4.2 \times 0.093) \div (4.2-0.093)=0.095$$

Given a 0.118M saline density of 1.003 gm/cm$^3$ (CRC Handbook of Chemistry and Physics, 61st Edition) a gel-layer thickness of 1.24 cm, a gel layer area of 28.27 cm$^2$, and a hydrostatic pressure of 4920 dyne/cm$^2$.

$$K=(0.095 \times 1.24)/(1.003 \times 28.27 \times 4920)-8.4 \times 10^{-7} \text{ cm}^3\text{sec/gm}$$

Considering the substantially constant flow rate and given a 0.118M saline viscosity of 0.01015 poise (CRC Handbook of Chemistry and Physics, 61st Edition):

$$x=K\eta=(8.4 \times 10^{-7}) \times 0.01015=8.6 \times 10^{-9} \text{ cm}^2$$

EXAMPLES

Examples 1 to 4 are examples of various absorbent article including absorbent bodies (cores) comprising in sequence an upper assembly that includes an upper acquisition layer and a superabsorbent layer and a lower assembly that includes an upper layer having void space for storage of liquid discharges and a lower layer which contains second superabsorbent material. Examples 1 to 3 are constructed broadly as illustrated diagrammatically in FIGS. 1a to 1c, wherein each of the superabsorbents is present as a thin preform layer.

In Example 4 the lower assembly comprises an air laid fibrous matrix wherein at least 70% by weight of the second superabsorbent material is in the lower half of the thickness of this matrix, and wherein there is a dusting layer, with a very low concentration of superabsorbent, on the lower face of the matrix.

From the GLP values quoted below it will be seen that Examples 3 and 4 at least are examples of the invention described above wherein the first superabsorbent has a GLP value of at least 4, and from the Dynamic Swelling Rate values it will be seen that Examples 1 to 3 at least are examples of absorbent bodies wherein the second superabsorbent material has a higher swelling rate and the first superabsorbent material has a substantially constant Dynamic Swelling Rate.

Table 1 quotes various quantitative values for the article. In this the article weight includes the weight of the topsheet, the containment tissue, the absorbent core, and the impervious backsheet. The fibre weight is the weight of all of the core fibres excluding tissue.

Table 2 quotes the content of the first acquisition layer and first superabsorbent layer in the upper assembly, and the second fibrous layer and the second superabsorbent layer in the lower assembly. In each instance there is quoted, in sequence, the nature of the material, the basis weight (grams per square meter) and the dimensions.

TABLE 1

| Example | Article Weight (g) | Core Area (cm$^2$) | Fibre Weight (g) | Fibre Capacity (ml) | Super-absorbent Weight (g) | Super-absorbent Capacity (ml) | Total Article capacity (ml) | Theoretical Basis Capacity (ml cm$^{-2}$) |
|---|---|---|---|---|---|---|---|---|
| 1 | 31 | 213 | 10.5 | 33.00 | 15.00 | 465.00 | 498.00 | 2.34 |
| 2 | 27 | 213 | 12.5 | 37.50 | 9.80 | 295.00 | 332.50 | 1.56 |
| 3 | 31 | 337 | 14.3 | 34.00 | 8.50 | 264.00 | 298.00 | 0.89 |
| 4 |  | 25 | 188 | 10.2 | 32 | 275 | 307 | 1.63 |

TABLE 2

| Example | 1st Acquisition Layer | 1st Superabsorbent Layer | 2nd Fibrous Layer | 2nd Superabsorbent Layer |
|---|---|---|---|---|
| 1 | CCLC<br>294<br>25 cm × 7.5 cm | SX-MW 20/30<br>267<br>25 cm × 7.5 cm | CCLC<br>294<br>25 cm × 7.5 cm | SX-MW 60/100<br>533<br>25 cm × 7.5 cm |
| 2 | CCLC<br>294<br>25 cm × 8.5 cm | SMX 300 (5)<br>160<br>25 cm × 7.5 cm | CCLC<br>294<br>25 cm × 7.5 cm | SXM-W 60/100<br>320<br>25 cm × 7.5 cm |
| 3 | CCLC<br>280<br>25 cm × 7.5 cm | L76lf 20/30 (6)<br>100<br>25 cm × 7.5 cm | CCLC<br>280<br>45 cm × 7.5 cm | L76if 60/100<br>240<br>45 cm × 7.5 cm |
| 4 | CCLC<br>272<br>25 cm × 7.5 cm | SX-P<br>160<br>25 cm × 7.5 cm | CCLC<br>272<br>25 cm × 7.5 cm | SX-P<br>362<br>25 cm × 7.5 cm |

CCLC is chemically cross-linked cellulose, for example as described in U.S. Pat. No. 4,898,642.

SX-MW 20/30 is Favor SX/MW from Stockhausen GmbH having a particle size distribution of 20/30 mesh (600 to 850 μm) an AAP value of 20 g/g at 0.7 psi, a Dynamic Swelling Rate of 0.16 g/sec and which is linear and a substantially non-decreasing value.

SX/MW 60/100 is the 60/100 mesh (150 to 250 μm particle size fraction) of the same general type having AAP 20 g/g at 0.7 psi and DSR 0.24 g/g/sec.

SXM 300 is Favor SXM 300 from Stockhausen GmbH which is unsieved and which has AAP 21 g/g at 0.7 psi and a Dynamic Swelling Rate of below 0.1 g/g/sec and which is linear and substantially non-decreasing.

L761f is Aqualic CA L761f lot no. 2G18 obtained from Shokuba Ultrasorb. Fraction 20/30 has mesh size 20/30 (600 to 850 μm, AAP of 22 g/g, GLP of $4.5 \times 10^{-7}$ cm$^3$ sec/g and a Dynamic Swelling Rate that is linear and substantially non-decreasing and is 0.17 g/g/sec. Fraction 60/100 has AAP 20 g/g at 0.7 psi, low GLP and Dynamic Swelling Rate of 0.35 g/g/sec.

The performance of the four examples was compared against a number of different structures, including two of the applicants' commercial structures and a commercial structure of another major absorbent article manufacturer. The results are illustrated in Table 2.

Comparative Example 1 is an absorbent article having a core comprising airfelt only and including a topsheet and a backsheet. Comparative Example 2 is an absorbent article having a core comprising only chemically cross-linked cellulose as described above, and including a topsheet and a backsheet.

Comparative Example 3 is an absorbent article marketed under the trade name Pampers Baby Dry [Boy Maxi Size (8–18 kg)]. This product comprises a mixed airfelt/ superabsorbent core, having a patch of the same chemically cross-linked material as in comparative Example 2 located on top.

Comparative Example 4 is an absorbent article marketed under the trade name Pampers Phases. This product has a mixed airfelt/superabsorbent core.

Comparative Example 5 is an absorbent article that is marketed under the trade name Ultratrim (Boy Size 4 (10–16 kg)] by the Kimberley Clark Corporation. This product has a core that is an airfelt/superabsorbent mix.

Comparative Example 6 is an absorbent article made according to WO92/11831 and having a structure substantially identical to that of Example 2 but having a different superabsorbent material. The first and second (having double the basis weight of the first) superabsorbent materials are very "high-speed" gelling materials and comprise Norsolor X50 superabsorbent material (supplied by ELF ATOCHEM, Cedex, France). The first superabsorbent layer is 7.5 cm wide and has a 0.5 cm superabsorbent free stripe along each of its longitudinal sides, as described in WO92/11831.

Comparative Example 7 is an absorbent article made according to WO90/14815 and having a structure similar to that of Example 2 but having a tissue having a basis weight of 60 gm$^{-2}$ instead of CCLC as the second acquisition layer and having different superabsorbent materials. The first and second (having double the basis weight of the first) superabsorbent materials have different absorption rates and liquid retention abilities, and comprise respectively Aqualic CA W-4 (supplied by Nippon Shokubai Co. Ltd., Osaka, Japan) and Sanwet IM 5600S (supplied by Hoechst-Casella GmbH, Frankfurt, Germany).

Unless otherwise specified each of the topsheet and the backsheet used in the Examples and Comparative Examples is of the type described above.

TABLE 3

| | Design Structure | | | |
|---|---|---|---|---|
| | Article Weight (g) | Core Area (cm$^2$) | Theoretical Basis Capacity (ml cm$^{-2}$) | Pressure to achieve stack height of 9.00 mm (gcm$^{-2}$ (psi)) |
| Example | | | | |
| 1 | 31 | 213 | 2.34 | ≦200 (3) |
| 2 | 27 | 213 | 1.54 | ≦200 (3) |
| 3 | 21 | 337 | 0.89 | ≦200 (3) |
| 4 | 25 | 188 | 1.63 | ≦200 |
| Comparative Example | | | | |
| 1 | 44 | 800 | 0.20 | ≧350 (5) |
| 2 | 11 | 270 | 0.28 | ≦200 (3) |
| 3 | 37 | 750 | 0.45 | ≧350 (5) |
| 4 | 50 | 800 | 0.40 | ≧350 (5) |
| 5 | 40 | 600 | 0.67 | ≦200 (3) |
| 6 | 27 | 213 | 1.54 | ≦200 (3) |
| 7 | 22 | 213 | | ≦200 (3) |

TABLE 3-continued

| | Performance | | | | |
|---|---|---|---|---|---|
| | Acquisition Rate | X,Y-Demand Absorbency | | | Rewet at 50 |
| | at 50 gcm$^{-2}$ $^{(0.7}$ psi) at 50% Th. Cap. (ml s$^{-1}$) | $X_{90}$ (g g$^{-1}$) | $t_{90}$ (s) | $X_{90}/t_{90}$ (g g$^{-1}$ s$^{-1}$) | gcm$^{-3}$ (0.7 psi) at 75% Tg) Cap. |
| Example | | | | | |
| 1 | 1.0 | 17.0 | 300 | 0.060 | 0.25 |
| 2 | 1.8 | 13.0 | 94 | 0.140 | 0.15 |
| 3 | 1.5 | 14.5 | 270 | 0.054 | 0.50 |
| 4 | 1.1 | 17.7 | 395 | 0.045 | 0.1 |
| Comparative Example | | | | | |
| 1 | 1.2* | 4.0 | 35 | 0.120 | 10 |
| 2 | 6.9 | 6.7 | 15 | 0.045 | 17 |
| 3 | 1.3 | 14.2 | 410 | 0.035 | 0.20 |
| 4 | 0.82* | 12.8 | 610 | 0.022 | 0.70 |
| 5 | 0.46* | 15.6 | 820 | 0.019 | 0.80 |
| 6 | 1.3 | 16.7 | 225 | 0.075 | 0.70 |
| 7 | 0.62 | 18.6 | 1014 | 0.018 | 10.2 |

*at 25 g cm$^{-2}$ (0.35 psi)

A good core will ideally combine good performance and good design structure. It is generally not acceptable to provide a core having excellent performance, but which is very bulky and therefore not aesthetically pleasing, and which is also expensive to make and/or package.

The important parameters reflecting the advantages of the invention over the prior art, as represented by the comparative examples, are summarised in Table 2. Each parameter listed in that table represents only one specific benefit of the core of the invention to the user of an article incorporating the core, either throughout the article's lifetime or during a particular phase of its lifetime. The core of the invention exhibits good performance in a majority of the listed parameters, as compared with the comparative examples. More specifically the core of the invention generally exhibits:

1) A good acquisition rate (at least 1.0 ml s$^{-1}$) at 50% average theoretical basis capacity, which reflects good fluid absorption throughout the core's, and therefore the article's, in use lifetime;
2) A high fluid uptake value ($X_{90}/t_{90}$) of at least 0.05 g g$^{-1}$ s$^{-1}$ as measured by the X, Y-demand absorbency test, which indicates an efficient distribution mechanism within the core leading to efficient utilisation of storage capacity.
3) A low rewet (no greater than 0.6 g synthetic urine), which reflects superior skin dryness benefits for the user; and
4) A high capacity and average theoretical basis weight (at least 0.8 g g cm$^{-2}$) together with a low stack height (no greater than 9 mm), which allow the production of smaller and thinner efficient absorbent cores, and therefore articles, which are discrete in use, and which also save on packaging and transportation costs.

Only Example 6 of the comparative examples is satisfactory over most of the range of parameters. However Example 2 is a substantially identical structure to this comparative example and has superior performance to it with respect to both acquisition rate, rewet, and X, Y-demand absorbency properties, without the manufacturing complexities that tend to be required by the structure of Comparative Example 6 (as exemplified by the passages or pathways from upper storage layers to lower layers within the core structure). The superiority of the core of the invention in respect of these parameters is thought to be a result of a combination of the different fluid uptake rates of the superabsorbent materials together with their inclusion in the specific structure of the core of the invention.

We claim:

1. An absorbent body comprising in sequence from the top an upper assembly (3, 4, 5) that includes
    an upper acquisition layer (3) substantially free of superabsorbent material, and
    a superabsorbent layer (5) consisting mainly of first superabsorbent material which has a Gel Layer Permeability (GLP) value of at least about 4×10$^{-7}$ cm$^3$sec/g and which is present in an amount of at least about 20 g/m$^2$, and
    a lower assembly (6, 7, 8) that includes second superabsorbent material having an Absorption Against Pressure of at least 15 g/g at 50 g/cm$^2$ and which comprises
    an upper layer (6) having void space for storage of liquid discharges, and
    a lower layer (7) which contains second superabsorbent material and wherein at least 70% by weight of the total amount of the second superabsorbent material which is in the upper and lower layers is in the lower half of the combined thickness of the upper and lower layers.

2. An absorbent body according to claim 1 in which the GLP of the first superabsorbent material is at least 6×10$^{-7}$ cm$^3$sec/g.

3. An absorbent body according to claim 1 in which the GLP of the first superabsorbent material is at least 9×10$^{-7}$ cm$^3$sec/g.

4. An absorbent body according to claim 1 in which the first and second superabsorbent materials are the same material.

5. An absorbent body according to claim 1 in which the second superabsorbent material has a faster Dynamic Swelling Rate than the first superabsorbent material.

6. An absorbent body according to claim 5 in which the second superabsorbent material has a Dynamic Swelling Rate of at least 0.2 g/g/s.

7. An absorbent body according to claim 5 in which the second superabsorbent material has a Dynamic Swelling Rate which is at least 1.5 times the Dynamic Swelling Rate of the first superabsorbent material.

8. An absorbent body according to claim 1 in which of the upper and lower layers of the lower assembly are provided by an air laid fibrous matrix wherein at least 70% by weight of the second superabsorbent material is in the lower half of the thickness of the matrix.

9. An absorbent body according to claim 8 in which at least 5% of the second superabsorbent material is in the upper half of the thickness of the upper and lower layers.

10. An absorbent body according to claim 1 in which the upper and lower layers of the lower assembly are provided by air laying a blend of hydrophilic fibres and superabsorbent material.

11. An absorbent body according to claim 1 in which the air laid matrix additionally comprises a fibre layer substantially free of superabsorbent material which has been air laid with and beneath the lower layer.

12. An absorbent body according to claim 1 wherein the upper layer of the lower assembly is substantially free of superabsorbent material and the lower layer is a preformed layer comprising the superabsorbent material.

13. An absorbent body according to claim 12 in which the layer comprising the second superabsorbent material is a thin layer which consists substantially only of the second superabsorbent material.

14. An absorbent body according to claim 1 in which the amount of second superabsorbent material in the lower assembly is at least 30 to 95 (preferably 45 to 70%) by weight based on the total weight of the upper and lower storage layers and the amount of first superabsorbent material is 30 to 70% by weight the weight of the upper assembly.

15. An absorbent body according to claim 1 in which the upper acquisition layer has a wet compressibility of at least 5 $cm^3 g^{-1}$ and a drip capacity of 10 g $g^{-1}$.

16. An absorbent body according to claim 1 in which the acquisition layer is formed of first fibrous material which comprises at least 50% by weight chemically cross linked cellulosic fibres.

17. An absorbent body according to claim 1 having an average theoretical basis capacity of at least 0.8 ml $cm^{-2}$ and a stack height of not more than 9 mm at 200 g $cm^{-2}$.

18. An absorbent body according to claim 1 in which the first superabsorbent material is present as a preformed thin layer consisting substantially only of the superabsorbent material.

19. An absorbent body according to claim 1 comprising
   an upper assembly comprising an upper layer comprising a first porous material (3) having a wet compressibility of at least 5 $cm^3 g^{-1}$ and a drip capacity of at least 10 g $g^{-1}$, the assembly also comprising a first superabsorbent material (5) having a substantially non-decreasing Dynamic Swelling Rate and
   a lower assembly comprising a second porous material (6) and a second superabsorbent material (7) having a dynamic swelling rate of at least 0.2 g $g^{-1}s^{-1}$ and an absorption against pressure of at least 15 g $g^{-1}$ at 50 g $cm^{-2}$ (0.7 psi),
   wherein the Dynamic Swelling Rate of the second superabsorbent material is at least 1.5 times the Dynamic Swelling Rate of the second superabsorbent material.

20. An absorbent body comprising in sequence through its thickness from the top
   an upper assembly comprising an upper layer comprising a first porous material (3) having a wet compressibility of at least 5 $cm^3 g^{-1}$ and a drip capacity of at least 10 g $g^{-1}$, the assembly also comprising a first superabsorbent material (5) having a substantially non-decreasing Dynamic Swelling Rate and
   a lower assembly comprising a second porous material (6) and a second superabsorbent material (7) having a dynamic swelling rate of at least 0.2 g $g^{-1}s^{-1}$ and an absorption against pressure of at least 15 g $g^{-1}$ at 50 g $cm^{-2}$ (0.7 psi),
   wherein the Dynamic Swelling Rate of the second superabsorbent material is at least 1.5 times the Dynamic Swelling Rate of the second superabsorbent material.

21. An absorbent body according to claim 20 in which the first porous material is a fibrous material which comprises at least 50% by weight chemically cross linked cellulosic fibres.

22. An absorbent body according to claim 20 having an average theoretical basis capacity of at least 0.8 ml $cm^{-2}$ and a stack height of not more than 9 mm under a pressure of 200 g $cm^{-2}$.

23. An absorbent article comprising, in sequence, a liquid pervious topsheet, an absorbent body comprising, in sequence from the top:
   an upper assembly that includes:
      an upper acquisition layer substantially free of super absorbent material, and a super absorbent layer consisting mainly of first super absorbent layer which has a Gel Layer Permeability (GLP) value of at least about $4 \times 10^{-7}$ $cm^3$ sec/gm and which is present in an amount of at least about 20 g/m2, and
   a lower assembly that includes:
      a second superabsorbent material having an Absorbent Against Pressure of at least 15 g/g at 50 g/$cm^2$ and which comprises:
         an upper layer having void space for storage of liquid discharges, and
         a lower layer which contains second superabsorbent material and wherein at least 70% by weight of the total amount of the second superabsorbent material which is in the upper and lower layers is in the lower half of the combined thickness of the upper and lower layers, arranged with the upper acquisition layer towards the topsheet, and
   a liquid impervious backsheet.

24. An absorbent article according to claim 23 and which is a disposable diaper, incontinence article or training pant.

25. An absorbent article comprising, in sequence, a liquid pervious topsheet, an absorbent body comprising, in sequence through its thickness from the top:
   an upper assembly comprising:
      an upper layer comprising a first porous material having a wet compressibility of at least 5 $cm^3 g^{-1}$ and a drip capacity of at least 10 g/g, the assembly also comprising a first superabsorbent material having a substantially non-decreasing Dynamic Swelling Rate, and
   a lower assembly comprising:
      a second porous material and a second superabsorbent material having a dynamic swelling rate of at least 0.2 g/g/s and an absorption constant against pressure of at least 15 g/g at 50 g/$cm^2$ (0.7 psi),
      wherein the Dynamic Swelling Rate of the second superabsorbent material is at least 1.5 times the Dynamic Swelling Rate of the second superabsorbent material, arranged with the upper layer towards the topsheet and
   a liquid impervious backsheet.

26. An absorbent article according to claim 25 and which is a disposable diaper, incontinence article or training pant.

* * * * *

UNITED STATES PATENT AND TRADEMARK OFFICE
CERTIFICATE OF CORRECTION

PATENT NO.    : 5,836,929
DATED         : November 17, 1998
INVENTOR(S)   : Christopher Phillip Bewick-Sonntag et al.

It is certified that error appears in the above-identified patent and that said Letters Patent is hereby corrected as shown below:

Column 3,
Line 5, delete "15,x$10^{-7}$ cm$^3$sec/g" and insert -- 15x$10^{-7}$ cm$^3$ sec/g --.

Column 5,
Line 38, delete "non-stiffened" and insert -- nonstiffened --.
Line 42, delete "cross-linking" and insert -- crosslinking --.

Column 7,
Line 39, delete "40,x$10^{-7}$ cm$^3$ sec/g" and insert -- 40x$10^{-7}$ cm$^3$ sec/g --.

Column 10,
Line 13, delete "6,x$10^{-7}$ cm$^3$ sec/g)" and insert -- 6x$10^{-7}$ cm$^3$ sec/g) --.
Line 35, delete "pock-marking" and insert -- pockmarking --.
Line 66, delete "cross-linked," and insert -- crosslinked, --.

Column 11,
Line 32, delete "200 gcm$^{-2}$" and insert -- 200 g cm$^{-2}$ --.

Column 14,
Line 51, delete "2.0 g/:" and insert -- 2.0 g/l --.
Line 53, delete "ad 0.23" and insert -- and 0.23 --.

Column 17,
Line 51, delete "20 gcm$^{-2}$" and insert -- 20 g cm$^{-2}$ --.

Column 18,
Line 8, delete "(inunits of" and insert -- (in units of --.

Column 19,
Line 1, delete "(NH$_4$)$_2$HPO$_4$," and insert -- (NH$_4$)H$_2$PO$_4$, --.

Column 21,
Line 23, delete "Dusseldorf," and insert -- Düsseldorf, --.
Line 25, delete "VACUPACK$_2$ PLUS" and insert -- VACUPACK2 PLUS --.
Line 46, delete "initial force?]" and insert -- initial force]. --.
Line 49, delete "stabilised" and insert -- stabilized --.

Column 22,
Line 4, delete "Instrument." and insert -- Instrument --.

UNITED STATES PATENT AND TRADEMARK OFFICE
CERTIFICATE OF CORRECTION

PATENT NO. : 5,836,929
DATED : November 17, 1998
INVENTOR(S) : Christopher Phillip Bewick-Sonntag et al.

It is certified that error appears in the above-identified patent and that said Letters Patent is hereby corrected as shown below:

Column 24,
Line 41, delete "(ara=28.27 cm$^2$)," and insert -- (area=28.27 cm$^2$), --.

Column 25,
Line 29, delete "02. gm/sec," and insert -- 0.02 gm/sec, --.
Line 38, "(NH$_4$)$_2$HPO$_4$," and insert -- (NH$_4$)H$_2$PO$_4$, --.
Line 41, delete "0.118M" and insert -- 0.118 M --.

Column 26,
Line 32, delete "the. piston/" and insert -- the piston/ --.
Line 60, delete "is use" and insert -- is used --.

Column 27,
Line 46, delete "0.118M" and insert -- 0.118 M --.

Column 28,
Line 2, delete "0.118M" and insert -- 0.118 M --.

Column 29,
Line 63, delete "(Boy" and insert -- [Boy --.

Column 32,
Lines 13-14, delete "4x10$^{-7}$cm$^3$sec/g" and insert -- 4x10$^{-7}$ cm$^3$ sec/g --.
Lines 29-30, delete "6x10$^{-7}$cm$^3$sec/g." and insert -- 6x10$^{-7}$ cm$^3$ sec/g. --.
Lines 32-33, delete "9x10$^{-7}$cm$^3$sec/g." and insert -- 9x10$^{-7}$ cm$^3$ sec/g. --.

UNITED STATES PATENT AND TRADEMARK OFFICE
CERTIFICATE OF CORRECTION

PATENT NO. : 5,836,929
DATED : November 17, 1998
INVENTOR(S) : Christopher Phillip Bewick-Sonntag et al.

It is certified that error appears in the above-identified patent and that said Letters Patent is hereby corrected as shown below:

Column 34,
Line 15, delete "20 g/m2," and insert -- 20 g/m$^2$, --.

Signed and Sealed this

Thirteenth Day of June, 2006

JON W. DUDAS
*Director of the United States Patent and Trademark Office*